(12) United States Patent
Ohashi et al.

(10) Patent No.: US 10,971,673 B2
(45) Date of Patent: Apr. 6, 2021

(54) PIEZOELECTRIC ELEMENT, PIEZOELECTRIC DEVICE, ULTRASONIC PROBE AND ELECTRONIC APPARATUS

(71) Applicant: Seiko Epson Corporation, Tokyo (JP)

(72) Inventors: Koji Ohashi, Matsumoto (JP); Takahiro Kamijo, Matsumoto (JP); Katsuhiro Imai, Minowa (JP); Takumi Yamaoka, Chino (JP); Chikara Kojima, Matsumoto (JP)

(73) Assignee: Seiko Epson Corporation (JP)

( * ) Notice: Subject to any disclaimer, the term of this patent is extended or adjusted under 35 U.S.C. 154(b) by 563 days.

(21) Appl. No.: 15/935,539

(22) Filed: Mar. 26, 2018

(65) Prior Publication Data
US 2018/0277738 A1    Sep. 27, 2018

(30) Foreign Application Priority Data
Mar. 27, 2017    (JP) .............................. JP2017-061440

(51) Int. Cl.
*H01L 41/047*    (2006.01)
*H01L 41/053*    (2006.01)
(Continued)

(52) U.S. Cl.
CPC ............ *H01L 41/0475* (2013.01); *A61B 8/06* (2013.01); *A61B 8/12* (2013.01); *B06B 1/0215* (2013.01);
(Continued)

(58) Field of Classification Search
CPC combination set(s) only.
See application file for complete search history.

(56) References Cited

U.S. PATENT DOCUMENTS 10,029,462 B2 *    7/2018    Kimura .................. H01L 41/04
2002/0105250 A1    8/2002    Klee et al.
(Continued)

FOREIGN PATENT DOCUMENTS

JP    11-017239 A    1/1999
JP    2008-284781 A    11/2008
(Continued)

OTHER PUBLICATIONS

Extended European Search Report for EP Application No. 18163588.9, dated Sep. 6, 2018 (6 pages).

*Primary Examiner* — Bryan P Gordon
(74) *Attorney, Agent, or Firm* — Harness, Dickey & Pierce, P.L.C.

(57) ABSTRACT

A piezoelectric element has a first electrode layer, a piezoelectric layer on the first electrode layer, a second electrode layer on the piezoelectric layer, a third electrode layer on part of the second electrode layer and including third metal, and an insulating layer covering at least a part of the piezoelectric layer not provided with the second electrode layer and having an aperture exposing a part of the second electrode layer. The second electrode layer has a first layer including first metal and a second layer including second metal on the first layer. The second layer is exposed in the aperture. A difference in standard redox potential between the second metal and the third metal is smaller than a difference in standard redox potential between the first metal and the third metal.

20 Claims, 15 Drawing Sheets

(51) Int. Cl.
*H01L 41/187* (2006.01)
*H01L 41/09* (2006.01)
*H01L 41/29* (2013.01)
*B06B 1/06* (2006.01)
*G01N 29/24* (2006.01)
*A61B 8/12* (2006.01)
*A61B 8/06* (2006.01)
*B06B 1/02* (2006.01)
*B41J 2/14* (2006.01)

(52) U.S. Cl.
CPC ............ *B06B 1/067* (2013.01); *B06B 1/0622* (2013.01); *G01N 29/245* (2013.01); *H01L 41/047* (2013.01); *H01L 41/0477* (2013.01); *H01L 41/0533* (2013.01); *H01L 41/09* (2013.01); *H01L 41/0973* (2013.01); *H01L 41/1876* (2013.01); *H01L 41/29* (2013.01); *B06B 2201/76* (2013.01); *B41J 2/14201* (2013.01)

(56) References Cited

U.S. PATENT DOCUMENTS

| | | |
|---|---|---|
| 2014/0253641 A1 | 9/2014 | Furuya |
| 2014/0267504 A1* | 9/2014 | Ohashi ................ B41J 2/14233 347/68 |
| 2016/0043299 A1* | 2/2016 | Fujimori ............. H01L 41/0805 310/330 |
| 2016/0345932 A1* | 12/2016 | Miyazawa ............. A61B 8/461 |
| 2017/0155028 A1* | 6/2017 | Kiyose ................ H01L 41/0474 |

FOREIGN PATENT DOCUMENTS

| | | |
|---|---|---|
| JP | 2011-230346 A | 11/2011 |
| JP | 2012-051325 A | 3/2012 |
| JP | 2014-141098 A | 8/2014 |
| JP | 2014-172178 A | 9/2014 |
| JP | 2014-175577 A | 9/2014 |
| JP | 2014-195494 A | 10/2014 |

* cited by examiner

PIEZOELECTRIC ELEMENT, PIEZOELECTRIC DEVICE, ULTRASONIC PROBE AND ELECTRONIC APPARATUS

BACKGROUND

1. Technical Field

The present invention relates to a piezoelectric element, a piezoelectric device, an ultrasonic probe, and an electronic apparatus.

2. Related Art

In the past, there has been known a piezoelectric element provided with a first electrode, a piezoelectric layer disposed on the first electrode, a second electrode disposed on the piezoelectric layer, and a protective film covering at least a part of the first electrode, the piezoelectric layer and the second electrode (see, e.g., JP-A-2014-175577).

In the piezoelectric element of JP-A-2014-175577, the protective film is formed continuously from the first electrode through the second electrode so as to cover side surfaces of the piezoelectric layer. In such a configuration, it is possible to prevent the piezoelectric layer from burning out at a boundary between the first electrode and the piezoelectric layer and a boundary between the second electrode and the piezoelectric layer due to the energization between the first electrode and the second electrode. Further, a penetrating part is formed in a part of the protective film covering the second electrode, and a leading electrode for inputting a drive signal to the second electrode is connected to the second electrode via the penetrating part.

Incidentally, in order to prevent the protective film from hindering the displacement of the piezoelectric element in JP-A-2014-175577, there is formed an opening in a part of the protective film corresponding to an active section in which the first electrode, the piezoelectric layer, and the second electrode overlap one another.

However, in such a configuration, since the second electrode is exposed from the opening, if metal that is higher in ionization tendency than the constituent metal of the second electrode is used as the leading electrode, then there is a possibility that electromigration may occur when forming the leading electrode, and thus the performance of the piezoelectric element could be deteriorated.

For example, in the case of forming the leading electrode, an Au layer having a NiCr layer as a foundation layer is deposited on one surface (the surface on which the first layer, the piezoelectric layer, the second electrode and the protective layer are formed) of a substrate, and then, patterning is performed thereon with wet etching. In the configuration of JP-A-2014-175577, since the opening is disposed in apart of the second electrode, the second electrode has contact with the etchant through the opening during patterning. In this case, if metal (e.g., Ir) that is lower in ionization tendency than Ni and Cr is used as the second electrode, then there is a possibility that the electromigration occurs in the NiCr layer during the patterning to cause separation of the Au layer, and there is a problem that the performance of the piezoelectric element could be deteriorated due to a breakage of the leading electrode and an increase in electrical resistance of the leading electrode.

SUMMARY

An advantage of the invention is to provide a piezoelectric element, a piezoelectric device, an ultrasonic probe, and an electronic apparatus each having superior performance.

A piezoelectric element according to a first application example of the invention has a first electrode layer, a piezoelectric layer, and a second electrode layer stacked in sequence on one another, and includes a third electrode layer stacked on apart of the second electrode layer and including third metal, and an insulating layer covering at least a part of the piezoelectric layer not provided with the second electrode layer and having an aperture exposing a part of the second electrode layer, wherein the second electrode layer has a first layer including first metal and a second layer including second metal stacked in sequence on one another, the second layer being exposed in the aperture, and a difference in standard redox potential between the second metal and the third metal is smaller than a difference in standard redox potential between the first metal and the third metal.

In this application example, since the insulating layer is disposed in the part on which the second electrode layer of the piezoelectric layer is not stacked, the deterioration due to burning out of the piezoelectric layer can be prevented. Further, the insulating layer covers the second electrode except the part (conductive part) to which the third electrode layer is provided and the aperture of the second electrode layer. Further, since the second electrode layer has a configuration having the first layer and the second layer stacked on one another, the second layer is exposed in the aperture and the conductive part. Therefore, a configuration is obtained in which the first layer in the second electrode layer is covered by the insulating layer or the second layer, and is not exposed to the outside.

Further, the third electrode layer is disposed so as to have contact with the second layer in the conductive part of the second electrode layer, and the difference (absolute value) in standard redox potential between the second metal and the third metal is smaller than the difference (absolute value) in standard redox potential between the first metal and the third metal.

In such a configuration, when forming, for example, the third electrode layer, even in the case in which both the third electrode layer and the second electrode layer have contact with the liquid phase, the first layer is covered by the second layer or the insulating layer, and therefore does not have contact with the liquid phase. Therefore, the electromigration of the third metal of the third electrode layer can be suppressed. Therefore, in the case of, for example, using the third electrode layer as the leading electrode to be connected to the second electrode layer, an increase in electrical resistance and breaking of the interconnections due to the separation of the third electrode can be suppressed. Thus, it is possible to input the drive signal of a desired drive voltage to the piezoelectric element, and thus, the piezoelectric element high in performance can be provided.

In the piezoelectric element according to the application example, it is preferable that the difference (absolute value) in standard redox potential between the second metal and the third metal is one of equal to and smaller than a first value.

Here, the first value is an upper limit of the difference (absolute value) in standard redox potential between the second metal and the third metal with which the influence of electromigration is allowable even if the electromigration occurs in the second layer and the third electrode layer. The first value is a value with which the separation of the third metal layer is suppressed to the extent in which the sufficient function as the piezoelectric element can be kept even in the case in which the third metal layer is separated in the case of, for example, patterning the third electrode layer using wet etching, and can set using the etching time or the like.

In the case in which, for example, the etching time is long, the influence of the electromigration becomes significant, and therefore, the first value becomes smaller.

In the application example with the configuration described above, by making the difference (absolute value) in standard redox potential between the second metal and the third metal equal to or smaller than the first value, it is possible to provide a high performance piezoelectric element with the influence of the electromigration in the second layer and the third layer suppressed.

In the piezoelectric element according to the application example, it is preferable that the second metal is lower in standard redox potential than the third metal.

Incidentally, in order to improve the drive characteristics of the piezoelectric element, it is preferable to avoid stacking a member hindering the drive of the piezoelectric element as much as possible. In the application example with the configuration described above, by providing the aperture to the element main body having the first electrode layer, the piezoelectric element, and the second electrode layer overlap each other in the plan view viewed from the stacking direction of the first electrode layer, the piezoelectric element, and the second electrode layer, the deterioration of the drive characteristics of the piezoelectric element is suppressed.

Here, in the case in which the aperture size of the aperture is large (the exposure area of the second layer is large), and the ionization tendency of the third metal is higher than the ionization tendency of the second metal, there is a possibility that the electromigration of the third layer is advanced. In contrast, in the application example with the configuration described above, the ionization tendency of the second metal is higher than the ionization tendency of the third metal. In other words, the standard redox potential of the second metal is lower than the standard redox potential of the third metal. Therefore, even in the case in which the exposure area of the second layer is large, the electromigration of the third metal can be suppressed, and thus, the performance deterioration of the piezoelectric element due to the separation of the third electrode layer can be suppressed.

In the piezoelectric element according to the application example, it is preferable that the first metal is one species selected from a group consisting of iridium (Ir), platinum (Pt), and gold (Au), or an alloy of two or more species selected from the group, the second metal is one species selected from a group consisting of titanium (Ti), zirconium (Zr), manganese (Mn), tantalum (Ta), and zinc (Zn), or an alloy of two or more species selected from the group, and the third metal is one species selected from a group consisting of nickel (Ni), chromium (Cr), iron (Fe), cadmium (Cd), and cobalt (Co), or an alloy of two or more species selected from the group. In these metal materials, the difference (absolute value) in standard redox potential between the second metal and the third metal is smaller than the difference (absolute value) in standard redox potential between the first metal and the third metal. Further, the standard redox potential of the second metal is lower than the standard redox potential of the third metal. Thus, it is possible to provide a high performance piezoelectric element with the influence of the electromigration in the second layer and the third layer suppressed.

In the piezoelectric element according to the application example, it is preferable that the first metal is iridium (Ir), the second metal is titanium (Ti), and the third metal is an alloy of nickel (Ni) and chromium (Cr).

In the application example with this configuration, there are used Ir as the first metal, Ti as the second metal, and the alloy of Ni and Cr as the third metal. Ir has superior scientific stability in a broad pH range and abroad temperature range, and is particularly favorable in the case of performing etching when forming the piezoelectric element having a thin-film shape. Incidentally, in the case of forming the leading electrode, it is preferable to use Au low in electrical resistance, and in order to increase adhesiveness of Au with respect to the second electrode, the alloy of Ni and Cr is used as a foundation layer. Here, the differences (absolute values) between the standard redox potential of Ti and the standard redox potentials of Ni and Cr are smaller than the differences (absolute values) between the standard redox potential of Ir and the standard redox potentials of Ni and Cr. Further, the standard redox potential of Ti is lower than the standard redox potentials of Ni and Cr. Thus, the electromigration of Ni and Cr can be suppressed.

In the piezoelectric element according to the application example, it is preferable that the insulating layer is made of aluminum oxide, the piezoelectric layer is metal oxide having ferroelectricity, and a thickness of the second layer is no thicker than 8 nm.

In the application example with this configuration, aluminum oxide ($Al_2O_3$) is used as the insulating layer. Such an insulating layer using $Al_2O_3$ is superior in insulating property, heat resistance property, and mechanical strength, and is favorable as the insulating layer used for the piezoelectric element. In contrast, in the case of forming the insulating layer made of $Al_2O_3$, hydrogen is generated during the formation in some cases. The hydrogen thus generated is occluded by the titanium in the second layer, and if the hydrogen thus occluded impregnated in the piezoelectric layer, there is a possibility that the performance of the piezoelectric element deteriorates. In contrast, in the application example with the configuration described above, the thickness of the second layer is equal to or less than 8 nm, and in this case, the performance deterioration of the piezoelectric element due to the hydrogen occluded in the second layer can be suppressed.

A piezoelectric device according to an application example of the invention includes the piezoelectric element described above, and a drive section driven by the piezoelectric element.

The piezoelectric device according to this application example makes the piezoelectric element drive the drive section. Here, as described above, in the piezoelectric element, the first layer of the second electrode layer is covered by either the insulating layer or the second layer, and is not exposed to the outside. Further, the difference (absolute value) in standard redox potential between the second metal included in the second layer and the third metal included in the third electrode layer is smaller than the difference (absolute value) in standard redox potential between the first metal and the third metal. Therefore, the separation of the third electrode layer due to the electromigration of the third metal is suppressed, and thus, the performance of the piezoelectric element can be improved, and by extension, the performance of the piezoelectric device can also be improved.

In the piezoelectric device according to the application example, it is preferable that the drive section is a vibrating film.

In the application example with this configuration, by a vibrating part being driven (vibrated) by the piezoelectric element, it is possible to transmit the ultrasonic wave. Further, by detecting a potential difference between the first electrode layer and the second electrode layer of the piezoelectric element when the ultrasonic wave is received by the vibrating part, and the vibrating part is vibrated, it is possible to detect reception of the ultrasonic wave.

An ultrasonic probe according to an application example of the invention includes the piezoelectric device described above, and a housing adapted to house (holding) the piezoelectric device.

In the ultrasonic probe according to this application example, such an ultrasonic device as described above is housed in the housing, and by making the ultrasonic probe have contact with the test object, the ultrasonic measurement on the test object can be performed. Further, as described above, the piezoelectric device is formed of the high performance piezoelectric element, and in the ultrasonic probe equipped with the piezoelectric device, it is possible to perform highly accurate ultrasonic measurement.

An electronic apparatus according to an application example of the invention includes the piezoelectric device described above, and a controller configured to control the piezoelectric device.

In the electronic apparatus according to this application example, a variety of ultrasonic processes using the piezoelectric device can be performed. For example, in the case of using the piezoelectric device as the ultrasonic device for performing transmission and reception of an ultrasonic wave, it is possible to perform the transmission and the reception of the ultrasonic wave from the piezoelectric device to the test object to form an internal tomographic image of the test object, and to measure the state (e.g., the blood pressure and the blood flow of a living body) of a part of the test object. Further, by transmitting the ultrasonic wave to an affected area of the test object, it is possible to treat (perform an ultrasonic treatment on) the affected area, or to remove an elimination object attached to an object with the ultrasonic wave. Further, besides the transmission and the reception of the ultrasonic wave, the invention can also be implemented as a liquid jet apparatus as the electronic apparatus for making the piezoelectric device drive the drive section (the vibrating film) to thereby eject a liquid such as ink.

Further, since the electronic apparatus according to the application example is constituted by the piezoelectric element having the high performance described above, also in the electronic apparatus including the piezoelectric device constituted by the piezoelectric element, it is possible to perform the variety of ultrasonic processes described above with high accuracy.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

First Embodiment

An ultrasonic measurement apparatus according to an embodiment of the invention will hereinafter be described based on the accompanying drawings.

Figure 1:
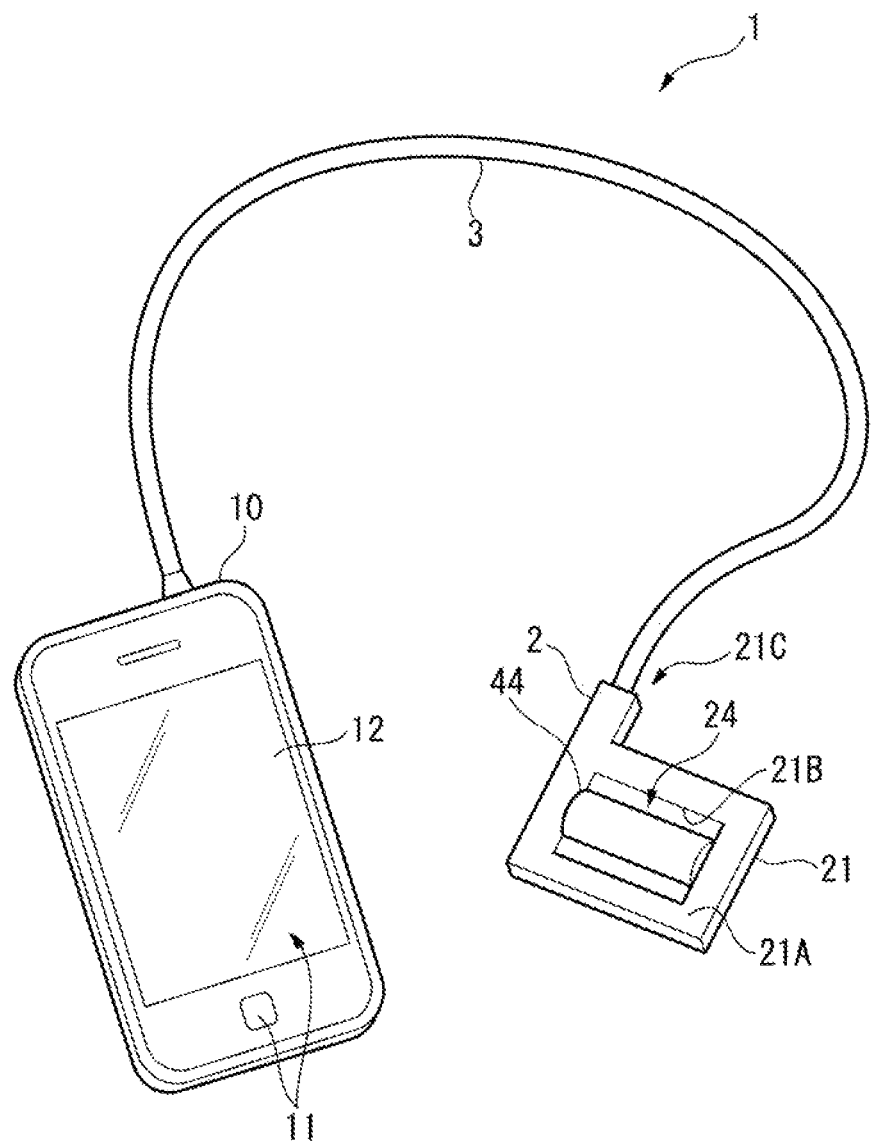
FIG. 1 is a perspective view showing a schematic configuration of an ultrasonic measurement apparatus according to a first embodiment of the invention.

FIG. 1 is a perspective view showing a schematic configuration of the ultrasonic measurement apparatus 1.

As shown in FIG. 1, the ultrasonic measurement apparatus 1 (an electronic apparatus) includes an ultrasonic probe 2 and a control device 10 (a control section or controller) electrically connected to the ultrasonic probe 2 via a cable 3.

The ultrasonic measurement apparatus 1 transmits an ultrasonic wave from the ultrasonic probe 2 to the inside of a test object (e.g., a living body such as a human body) with the ultrasonic probe 2 having contact with a surface of the test object. Further, the ultrasonic measurement apparatus 1 receives the ultrasonic wave reflected by an organ in the living body using the ultrasonic probe 2, and then, for example, obtains an internal tomographic image of the inside of the living body to measure the state (e.g., blood flow) of the organ in the living body based on the received signal.

Configuration of Control Device 10

As shown in FIG. 1, the control device 10 corresponds to a control section or controller, and includes an operating section 11 (an input) including buttons or touch panel, and a display 12. Further, although not shown in the drawings, the control device 10 includes a storage section formed of a memory, and an arithmetic section constituted by a central processing unit (CPU), processor or the like. The control device 10 makes the arithmetic section execute a variety of programs stored in the memory to thereby control the ultrasonic measurement apparatus 1. For example, the control device 10 outputs a command for controlling the drive of the ultrasonic probe 2, forms an image of the internal structure of the living body and then makes the display 12 display the image, and measures the living body information such as the blood flow to make the display 12 display the living body information based on the received signal input from the ultrasonic probe 2. Examples of such a control device 10 include a terminal device such as a tablet terminal, a smartphone, or a personal computer, and a dedicated terminal device for operating the ultrasonic probe 2 can also be used.

Configuration of Ultrasonic Probe 2

Figure 2:
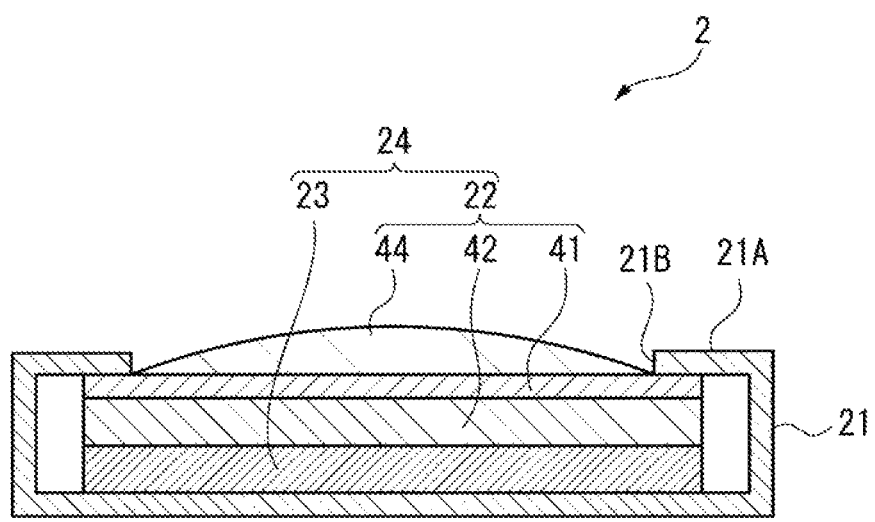
FIG. 2 is a cross-sectional view showing a schematic configuration of an ultrasonic probe according to the first embodiment.

FIG. 2 is a cross-sectional view showing a schematic configuration of the ultrasonic probe 2.

As shown in FIG. 2, the ultrasonic probe 2 includes a housing 21, an ultrasonic device 22 (a piezoelectric device) housed inside the housing 21, and a circuit board 23 provided with a driver circuit for controlling the ultrasonic device 22. It should be noted that the ultrasonic device 22 and the circuit board 23 constitute an ultrasonic sensor 24.

Configuration of Housing 21

As shown in FIG. 1, the housing 21 is formed to have a box-like shape having, for example, a rectangular planar shape, and on one surface (a sensor surface 21A) perpendicular to the thickness direction, there is formed a sensor window 21B, and a part of the ultrasonic device 22 is exposed therefrom. Further, in a part (a side surface in the example shown in FIG. 1) of the housing 21, there is provided a through hole 21C for the cable 3, and the cable 3 is connected to the circuit board 23 located inside the housing 21 through the through hole 21C. Further, the gap between the cable 3 and the through hole 21C is filled with, for example, a resin material to thereby ensure a waterproof property.

It should be noted that although in the present embodiment, there is shown a configuration example in which the ultrasonic probe 2 and the control device 10 are connected to each other using the cable 3, the configuration is not limited to this example, and it is also possible to, for example, connect the ultrasonic probe 2 and the control device 10 to each other with wireless communication, or to dispose a variety of constituents of the control device 10 inside the ultrasonic probe 2.

Configuration of Circuit Board 23

The circuit board 23 is electrically connected to signal terminals 413 and common terminals 414 (see FIG. 4 and FIG. 8) of the ultrasonic device 22 described later to control the ultrasonic device 22 based on the control by the control device 10.

Specifically, the circuit board 23 includes a transmission circuit and a reception circuit. The transmission circuit outputs a drive signal for making the ultrasonic device 22 perform ultrasonic transmission. The reception circuit obtains a reception signal output from the ultrasonic device 22, which has received the ultrasonic wave, then performs an amplification process, an A-D conversion process, and a phasing addition process of the reception signal, and then outputs the result to the control device 10.

Configuration of Ultrasonic Device 22

As shown in FIG. 2, the ultrasonic device 22 is configured with an element substrate 41, a sealing plate 42, an acoustic layer 43 (see FIG. 5 and FIG. 6), and an acoustic lens 44.

Configuration of Element Substrate 41

Figure 3:
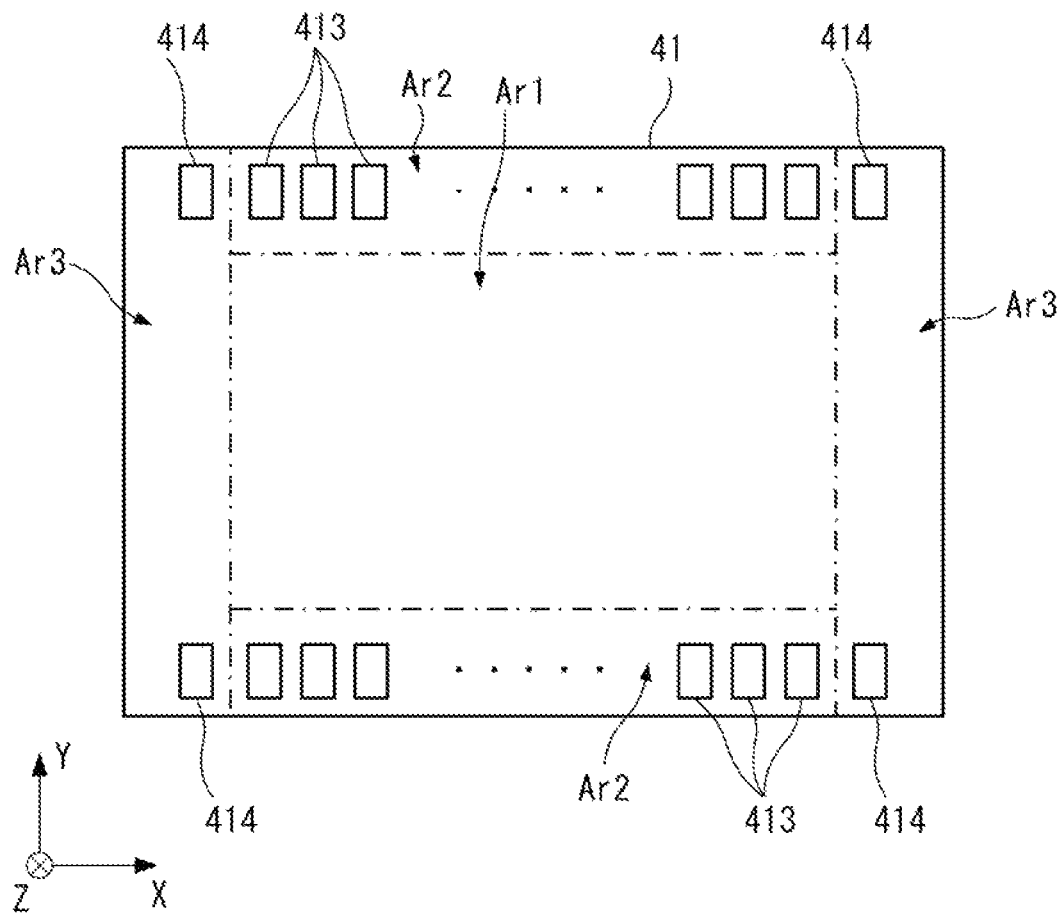
FIG. 3 is a plan view showing a schematic configuration of an element substrate in an ultrasonic device in the first embodiment.
Figure 4:
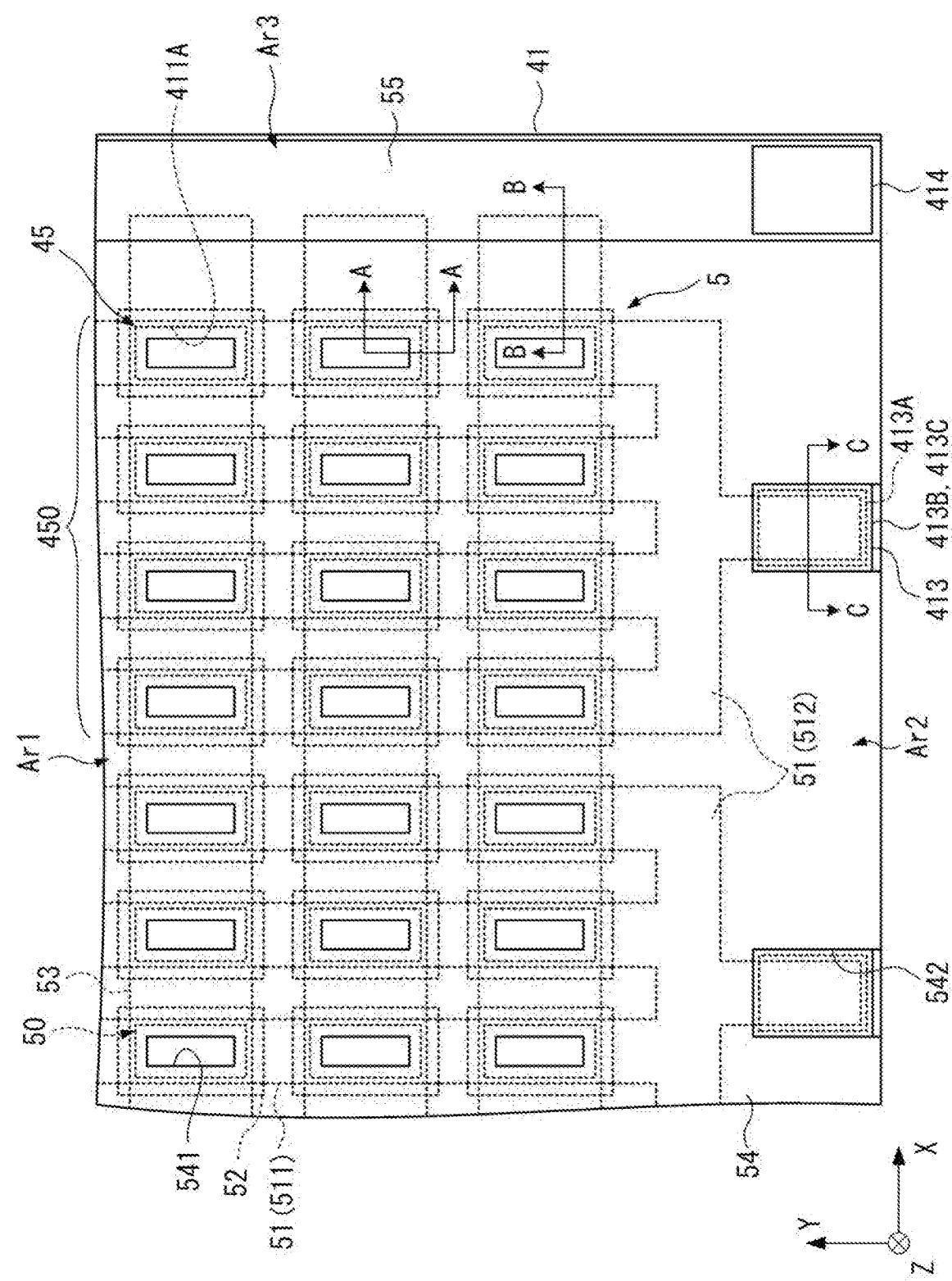
FIG. 4 is an enlarged plan view of a part of the element substrate of the first embodiment.
Figure 5:
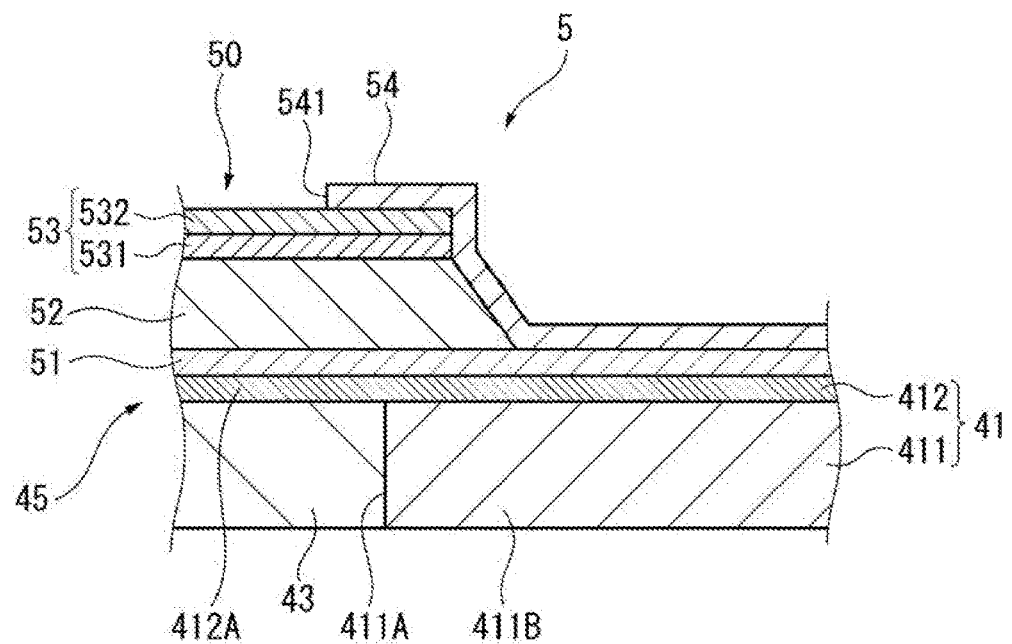
FIG. 5 is a schematic cross-sectional view of the ultrasonic device of the first embodiment cut along the line A-A shown in FIG. 4.
Figure 6:
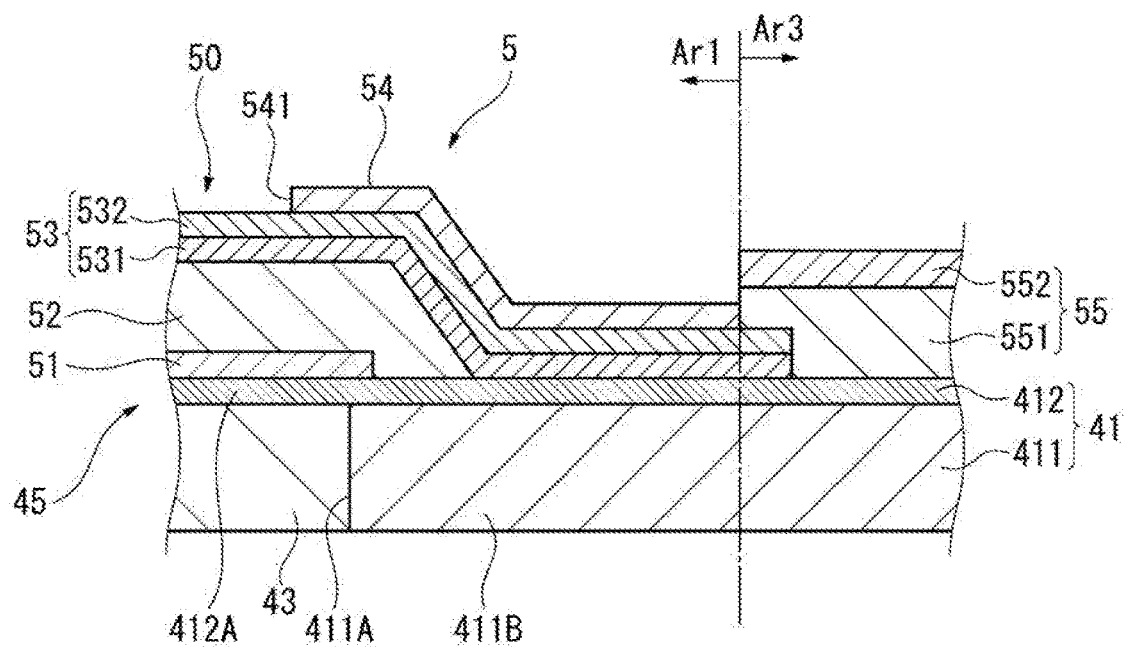
FIG. 6 is a schematic cross-sectional view of the ultrasonic device of the first embodiment cut along the line B-B shown in FIG. 4.
Figure 7:
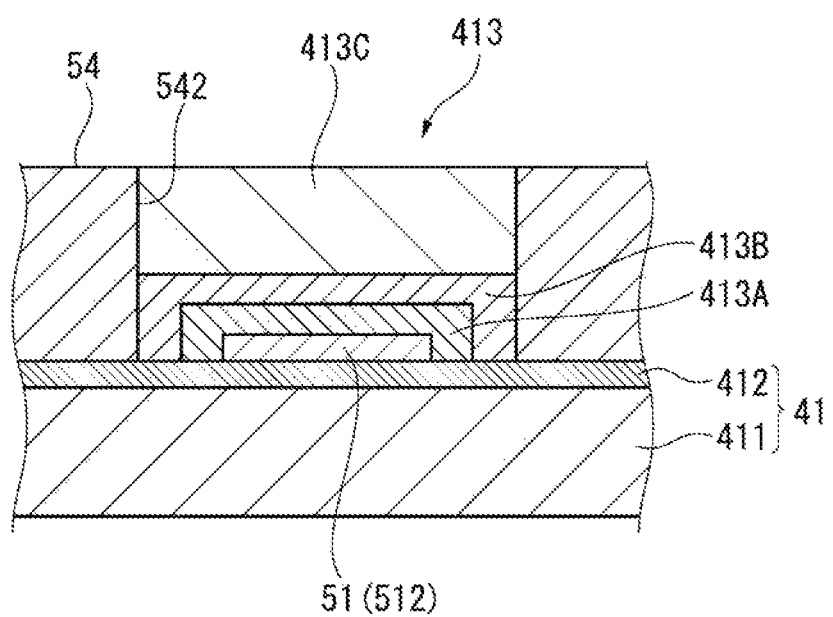
FIG. 7 is a schematic cross-sectional view of the ultrasonic device of the first embodiment cut along the line C-C shown in FIG. 4.
Figure 8:
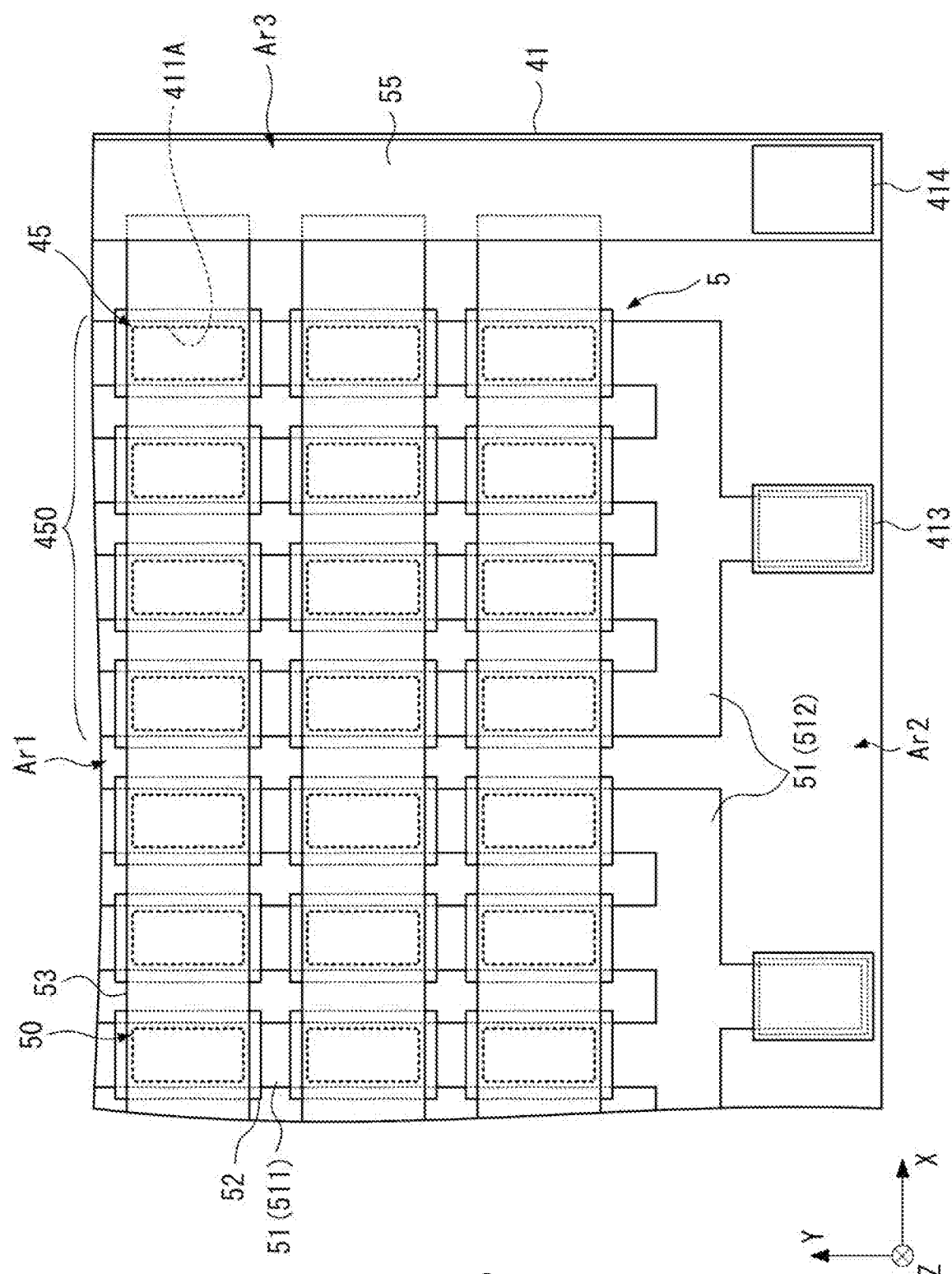
FIG. 8 is an enlarged plan view of a part of the element substrate with an insulating layer removed in FIG. 4.

FIG. 3 is a plan view showing a schematic configuration of an element substrate 41 constituting the ultrasonic device 22 when viewed from a sealing plate 42 side. FIG. 4 is an enlarged plan view showing a part (an end part on the +X side and the −Y side) of FIG. 3 in an enlarged manner. FIG. 5 is a schematic cross-sectional view of the ultrasonic device 22 cut along the line A-A shown in FIG. 4, FIG. 6 is a schematic cross-sectional view of the ultrasonic device 22 cut along the line B-B shown in FIG. 4, and FIG. 7 is a schematic cross-sectional view of the ultrasonic device 22 cut along the line C-C shown in FIG. 4. FIG. 8 is a plan view showing a schematic configuration of the element substrate 41 with an insulating layer 54 removed in FIG. 4.

As shown in FIG. 3, in a plan view of the element substrate 41 viewed from the substrate thickness direction (the Z direction) (hereinafter also referred to simply as a plan view), the element substrate 41 includes an array area Ar1, first terminal areas Ar2, and second terminal areas Ar3.

As shown in FIG. 4 and FIG. 8, in the array area Ar1, there is disposed a plurality of ultrasonic transducers 45 for performing transmission and reception of an ultrasonic wave. The plurality of ultrasonic transducers 45 is arranged in a matrix in the array area Ar1, and is configured as a one-dimensional array.

As shown in FIG. 4 and FIG. 8, in the present embodiment, a plurality of columns, each formed of the plurality of ultrasonic transducers 45 arranged along the Y direction (a slicing direction), is arranged along the X direction. Further, the four columns of the ultrasonic transducers 45 arranged along the X direction constitute a transmission/reception section 450 functioning as 1-CH transmission/reception channel. In other words, in the present embodiment, the element substrate 41 includes an ultrasonic array having a one-dimensional array structure in which a plurality of transmission/reception sections 450 is arranged in the X direction.

The first terminal areas Ar2 and the second terminal areas Ar3 are each an area where terminals for electrode interconnections to be connected to the respective transmission/reception sections 450 are arranged, and are disposed in the outer periphery of the array area Ar1.

More specifically, as shown in FIG. 5 and FIG. 6, the element substrate 41 includes a substrate main body part 411, and a vibrating film 412 (a drive section) disposed on the sealing plate 42 side (the −Z side) of the substrate main body part 411. Further, the vibrating film 412 includes a piezoelectric element 5.

The substrate main body part 411 is a substrate for supporting the vibrating film 412, and is formed of a semiconductor substrate made of, for example, Si. To the substrate main body part 411, there are provided substrate apertures 411A corresponding respectively to the ultrasonic transducers 45.

The vibrating film 412 is formed of, for example, $SiO_2$ or a stacked body of $SiO_2$ and $ZrO_2$, and is disposed on, for example, a surface (a back surface) on the sealing plate 42 side of the substrate main body part 411. The thickness of the vibrating film 412 becomes sufficiently small with respect to that of the substrate main body part 411. The vibrating film 412 is supported by partition walls 411B constituting the substrate apertures 411A, and closes the back surface side of the substrate apertures 411A. Here, in the vibrating film 412, a part (a part surrounded by the partition walls 411B) overlapping the substrate aperture 411A in the plan view constitutes a flexible part 412A. In other words, the substrate aperture 411A defines the outer edge of the flexible part 412A as a vibrating area of the vibrating film 412.

Further, on the surface of, for example, the sealing plate 42 side of the vibrator film 412, there is provided the piezoelectric element 5.

Configuration of Piezoelectric Element 5

As shown in FIG. 5 and FIG. 6, the piezoelectric element 5 includes a lower electrode 51 (a first electrode layer), a piezoelectric film 52 (a piezoelectric layer), an upper electrode 53 (a second electrode layer), an insulating layer 54, and a leading electrode 55 (a third electrode layer).

Here, in the piezoelectric element 5, a part of the lower electrode 51, a part of the piezoelectric film 52, and a part of the upper electrode 53 are stacked on the flexible part 412A in the order of the lower electrode 51, the piezoelectric film 52, and the upper electrode 53 to constitute an active section 50 (an element main body). The active section 50 deforms due to application of a voltage between the lower electrode 51 and the upper electrode 53. In the present embodiment, one flexible part 412A and the active section 50 provided to the flexible part 412A constitute one ultrasonic transducer 45. In other words, in the ultrasonic transducer 45, by applying a pulse-wave voltage with a predetermined frequency between the lower electrode 51 and the upper electrode 53, the active section 50 vibrates the flexible part 412A, and thus, an ultrasonic wave is transmitted. Further, when the reflected ultrasonic wave from the living body has been received, the flexible part 412A is vibrated, and a potential difference occurs between an upper part and a lower part of the active section 50. Further, by detecting the potential difference with the lower electrode 51 and the upper electrode 53, the reception of the ultrasonic wave is detected.

Configuration of Lower Electrode 51

As shown in FIG. 4 through FIG. 8, the lower electrode 51 is disposed on the vibrating film 412. As shown in FIG. 4 and FIG. 8, the lower electrode 51 includes lower electrode main body parts 511 and a lower electrode connection part 512.

The lower electrode main body parts 511 are each formed linearly throughout the plurality of ultrasonic transducers arranged in, for example, the Y direction in the plan view. In the present embodiment, the lower electrode main body parts 511 are each formed so as to be equal to or larger than the substrate aperture 411A (the flexible part 412A) in width in the X direction. In other words, in the present embodiment, the flexible part 412A is covered with the lower electrode main body part 511.

The lower electrode connection part 512 connects a plurality of (four columns in the present embodiment) lower electrode main body parts 511 to each other in, for example, both end parts (the −Y side end part is shown alone in FIG. 4) in the Y direction of each of the transmission/reception sections 450. Further, the lower electrode connection part 512 is disposed so as to extend from the array area Ar1 to the first terminal area Ar2, and is connected to the signal terminal 413 in the first terminal area Ar2.

Such a lower electrode 51 is formed of an electrically conductive material. The electrically conductive material is not particularly limited providing the electrically conductive material is a metal material, electrically conductive oxide, or a stacked material of theses materials. One of metal materials such as Ti, Pt, Ta, Ir, Sr, In, Sn, Au, Al, Fe, Cr, Ni, and Cu, and electrically conductive oxide represented by lanthanum-nickel oxide (LNO) alone, or a material obtained by combining or stacking two or more of these materials can also be used as the lower electrode 51.

Further, the signal terminal 413 connected to the lower electrode connection part 512 is constituted by a covering electrode 413A stacked on a part of the lower electrode connection part 512, a foundation electrode layer 413B, and a terminal electrode layer 413C.

As shown in FIG. 7, in the present embodiment, the covering electrode 413A is formed so as to cover a tip of the lower electrode connection part 512 disposed so as to extend from the array area Ar1 to the first terminal area Ar2. Further, the foundation electrode layer 413B is formed so as to cover the covering electrode 413A. Further, the terminal electrode layer 413C is formed so as to be stacked on the foundation electrode layer 413B.

Here, the covering electrode 413A is formed of the same material (e.g., Ti) as that of, for example, the second layer 532 described later.

Further, the foundation electrode layer 413B functions as a foundation layer of the terminal electrode layer 413C, and is formed of the same material (e.g., NiCr) as that of, for example, the first leading electrode layer 551 described later.

The terminal electrode layer 413C is formed using the foundation electrode layer 413B as a foundation, and is formed of the same material (e.g., Au) as that of, for example, the second leading electrode layer 552 described later.

Configuration of Piezoelectric Film 52

The piezoelectric film 52 has a roughly rectangular shape, and is disposed at a position where the piezoelectric film 52 overlaps the flexible part 412A in the plan view. The width in the X direction of the piezoelectric film 52 is larger than the width in the X direction of the substrate aperture 411A (the flexible part 412A), and is larger than the width in the X direction of the lower electrode main body part 511. In other words, the piezoelectric film 52 is disposed so as to cover the lower electrode main body part 511 with respect to the X direction. Further, the width in the Y direction of the piezoelectric film 52 is larger than the width in the Y direction of the substrate aperture 411A (the flexible part 412A), and is larger than the width in the Y direction of the upper electrode 53 described later.

The piezoelectric film 52 is, for example, a crystal film (a perovskite-type crystal) of oxide having a perovskite structure made of a ferroelectric ceramics material. In the present embodiment, a crystal film of lead zirconate titanate (PZT) is used as the piezoelectric film 52.

It should be noted that as the material of the piezoelectric film 52, there can be used, for example, a ferroelectric piezoelectric material such as lead zirconate titanate (PZT), a material obtained by adding metal oxide such as niobium oxide, nickel oxide, or magnesium oxide to the ferroelectric piezoelectric material. Specifically, there can be used lead titanate ($PbTiO_3$), lead zirconate titanate ($Pb(Zr, Ti)O_3$), lead zirconate ($PbZrO_3$), lead lanthanum titanate ((Pb, La), $TiO_3$), lead lanthanum zirconate titanate ((Pb, La) (Zr, Ti)$O_3$), lead zirconium titanate magnesium niobate (Pb(Zr, Ti) (Mg, Nb)$O_3$), or the like. In the present embodiment, lead zirconate titanate (PZT) is used as the piezoelectric film 52.

Further, the material of the piezoelectric film 52 is not limited to a lead-based piezoelectric material including lead, but it is also possible to use a non-lead-based piezoelectric material not including lead. As the non-lead-based piezoelectric material, there can be cited, for example, bismuth ferrate (($BiFeO_3$), "BFO" for short), barium titanate (($BaTiO_3$), "BT" for short), sodium potassium niobate ((K, Na) ($NbO_3$), "KNN" for short), lithium sodium potassium niobate ((K, Na, Li) ($NbO_3$)), lithium sodium potassium tantalate niobate ((K, Na, Li) (Nb, Ta)$O_3$), potassium bismuth titanate (($Bi_{1/2}Na_{1/2}$)$TiO_3$, "BKT" for short), sodium bismuth titanate (($Bi_{1/2}Na_{1/2}$)$TiO_3$, "BNT" for short), bismuth manganate ($BiMnO_3$, "BM" for short), composite oxide (x[($Bi_xK_{1-x}$)$TiO_3$]-(1-x) [$BiFeO_3$], "BKT-BF" for short) including bismuth, iron, barium, and titanium, and having the perovskite structure, composite oxide ((1-x) [($BiFeO_3$)-x[$BaTiO_3$], "BFO-BT" for short) including bismuth, iron, barium, and titanium, and having the perovskite structure, and a material ((1-x) [Bi($Fe_{1-y}M_y$)$O_3$]-x[$BaTiO_3$] (M denotes Mn, Co, or Cr)) obtained by adding metal such as manganese, cobalt, or chromium to these materials.

Configuration of Upper Electrode 53

As shown in FIG. 4 and FIG. 8, the upper electrode 53 has a linear shape parallel to the X direction in the plan view, and is formed throughout an area from the array area Ar1 to the second terminal area Ar3. Further, the upper electrode 53 connects the ultrasonic transducers 45 arranged along the X direction to each other, and functions as a common electrode in the ultrasonic transducers 45.

In the present embodiment, the upper electrode 53 is formed so as to be equal to or larger than the substrate aperture 411A (the flexible part 412A) in the width in the Y direction, and equal to or smaller than the piezoelectric film 52 in the width in the Y direction in the plan view.

Further, the upper electrode 53 includes a first layer 531 and a second layer 532, and is formed by stacking the first layer 531 and the second layer 532 in this order from the element substrate 41 side.

The first layer 531 is a metal layer which is formed of iridium (Ir) as first metal, or includes Ir. The second layer 532 is a metal layer which is formed of titanium (Ti) as second metal, or includes Ti.

Configuration of Insulating Layer 54

The insulating layer 54 is formed on roughly the entire surface from the array area Ar1 through the first terminal area Ar2 of the element substrate 41, and includes apertures in a part of the insulating layer 54.

Specifically, the insulating layer 54 has apertures 541 at positions where the apertures 541 overlap the center parts of the respective substrate apertures 411A (the flexible parts 412A) in the plan view, and the second layer 532 is exposed from the apertures 541. The aperture size of the aperture 541 is smaller than the size of the substrate aperture 411A (the flexible part 412A). In other words, the aperture edge of the aperture 541 is located more on an inner side than the aperture edge of the substrate aperture 411A.

Further, the insulating layer 54 has a terminal aperture 542 at a formation position of the signal terminal 413 in the first terminal area Ar2, and the signal terminal 413 is exposed from the terminal aperture 542.

It should be noted that as shown in FIG. 4, the insulating layer 54 is not formed in the second terminal area Ar3. Therefore, a part of the upper electrode 53 provided to the second terminal area Ar3 is not covered with the insulating layer 54.

The insulating layer 54 is formed using an insulating material having a water-resistant property such as aluminum oxide ($Al_2O_3$) or diamond-like carbon. Thus, the deterioration of the piezoelectric film 52 due to the moisture can be prevented. In particular, aluminum oxide ($Al_2O_3$) is superior in insulating property, heat resistance property, and mechanical strength, and is low in price and easy to manufacture, and is therefore preferably used. In the present embodiment, $Al_2O_3$ is used as the insulating layer 54.

Configuration of Leading Electrode 55

The leading electrode 55 is formed along the Y direction so as to form, for example, a linear shape in the second terminal area Ar3, and connects the end parts in the X direction of the upper electrodes 53 arranged in the Y direction to each other. Further, the leading electrode 55 is connected to the common terminal 414 in the second element area Ar3. It should be noted that although the leading electrode 55 in the +X side end part is shown alone in FIG. 4 and FIG. 8, it is also possible to adopt a configuration in which the leading electrodes 55 are disposed on both end parts of the array area Ar1 in the X direction.

As shown in FIG. 6, the leading electrode 55 includes a first leading electrode layer 551, and a second leading electrode layer 552.

The first leading electrode layer 551 is a layer including an alloy (NiCr) of nickel (Ni) and chromium (Cr) as third metal, or a layer formed of NiCr.

The second leading electrode layer 552 is a metal layer formed on the first leading electrode layer 551 using the first leading electrode layer 551 as a foundation layer, and is formed using, for example, Au low in electrical resistance.

Here, as described above, in the present embodiment, the upper electrode 53 is formed throughout an area from the array area Ar1 to the second terminal area Ar3, and the leading electrode 55 is formed so as to cover a part of the upper electrode 53 located in the second terminal area Ar3.

Therefore, all areas other than the aperture 541 of the upper electrode 53 are covered by the insulating layer 54 in the array area Ar1, and the upper electrode 53 is covered by the leading electrode 55 in the second terminal area Ar3. In other words, a configuration is obtained in which only the second layer 532 is exposed in a part overlapping the aperture 541 of the upper electrode 53 in the plan view, and the remainder is covered by the insulating layer 54 or the leading electrode 55. Therefore, the first layer 531 of the upper electrode 53 is not exposed to the outside.

Configuration of Sealing Plate 42

Referring back to FIG. 2, the sealing plate 42 will now be described.

As described above, the sealing plate 42 is bonded on the vibrating film 412 side of the element substrate 41. The sealing plate 42 is formed to have the same shape when viewed from the thickness direction as that of, for example, the element substrate 41, and is formed of a semiconductor substrate made of Si or the like, or an insulator substrate. It should be noted that the material and the thickness of the sealing plate 42 affect the frequency characteristics of the ultrasonic transducer 45, and are therefore preferably set based on the central frequency of the ultrasonic wave transmitted/received by the ultrasonic transducer 45.

The sealing plate 42 is bonded to the vibrating film 412 of the element substrate 41 with a bonding member not shown at positions overlapping the partition walls 411B in the array area Ar1, and in the first terminal area Ar2 and the second terminal area Ar3 of the element substrate 41 in the plan view.

Further, connections for connecting the signal terminals 413 and the common terminals 414 to the circuit board 23 are provided to the sealing plate 42 at positions opposed to the first terminal area Ar2 and the second terminal area Ar3 of the element substrate 41. As the connections, it is possible to illustrate, for example, through holes penetrating the sealing plate 42 in the thickness direction. In this case, it is possible to connect the terminals 413, 414 and the circuit board 23 with each other via the through holes with wiring members such as flexible printed circuits (FPC), cables, or wires. Further, it is also possible to provide through electrodes to the sealing plate 42 to thereby connect the terminals 413, 414 and the circuit board 23 to each other with the through electrodes.

Configuration of Acoustic Layer 43 and Acoustic Lens 44

As shown in FIG. 5 and FIG. 6, the substrate apertures 411A of the element substrate 41 are filled with the acoustic layer 43.

The acoustic lens 44 is disposed on the opposite side of the element substrate 41 (the +Z side) relative to the vibrating film 412, and is tightly fixed to the acoustic lens layer 43. The acoustic lens 44 presses against the living body surface as the test object when performing the ultrasonic measurement using the ultrasonic probe 2, and converges the ultrasonic wave, which has been transmitted from the ultrasonic transducer 45, inside the living body. Further, the acoustic lens 44 makes the ultrasonic wave, which has been reflected inside the living body, propagate to the ultrasonic transducer 45 via the acoustic layer 43.

The acoustic impedance of the acoustic layer 43 and the acoustic lens 44 is set to a value close to the acoustic impedance of the living body. Thus, it is possible for the acoustic layer 43 and the acoustic lens 44 to efficiently propagate the ultrasonic wave emitted from the ultrasonic transducer 45 to the living body, and further propagate the ultrasonic wave, which has been reflected inside the living body, to the ultrasonic transducer 45 with efficiency.

Method of Manufacturing Piezoelectric Element 5

Hereinafter, a method of manufacturing the piezoelectric element 5 will be described.

Figure 9:
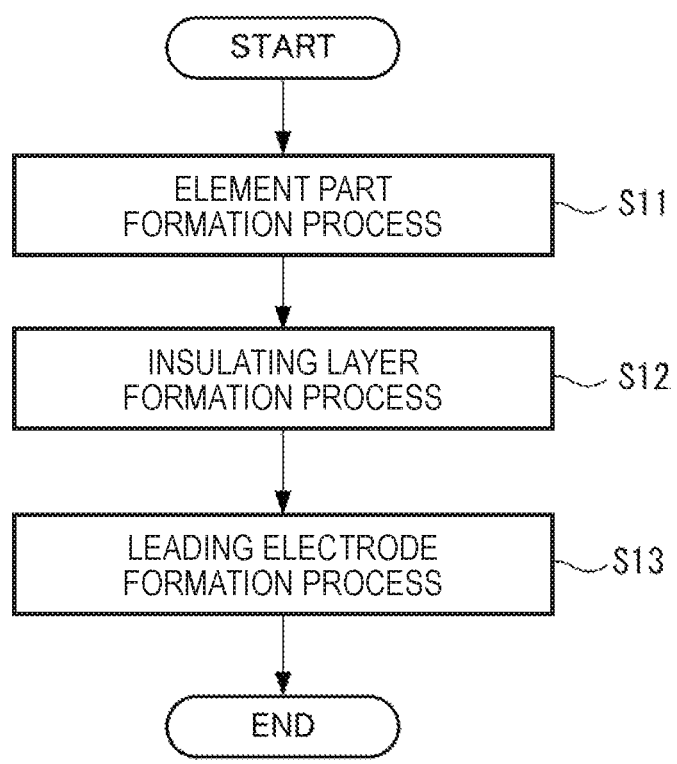
FIG. 9 is a flowchart showing a manufacturing method of a piezoelectric element according to the first embodiment.

FIG. 9 is a flowchart showing the method of manufacturing the piezoelectric element 5.

Figure 10:
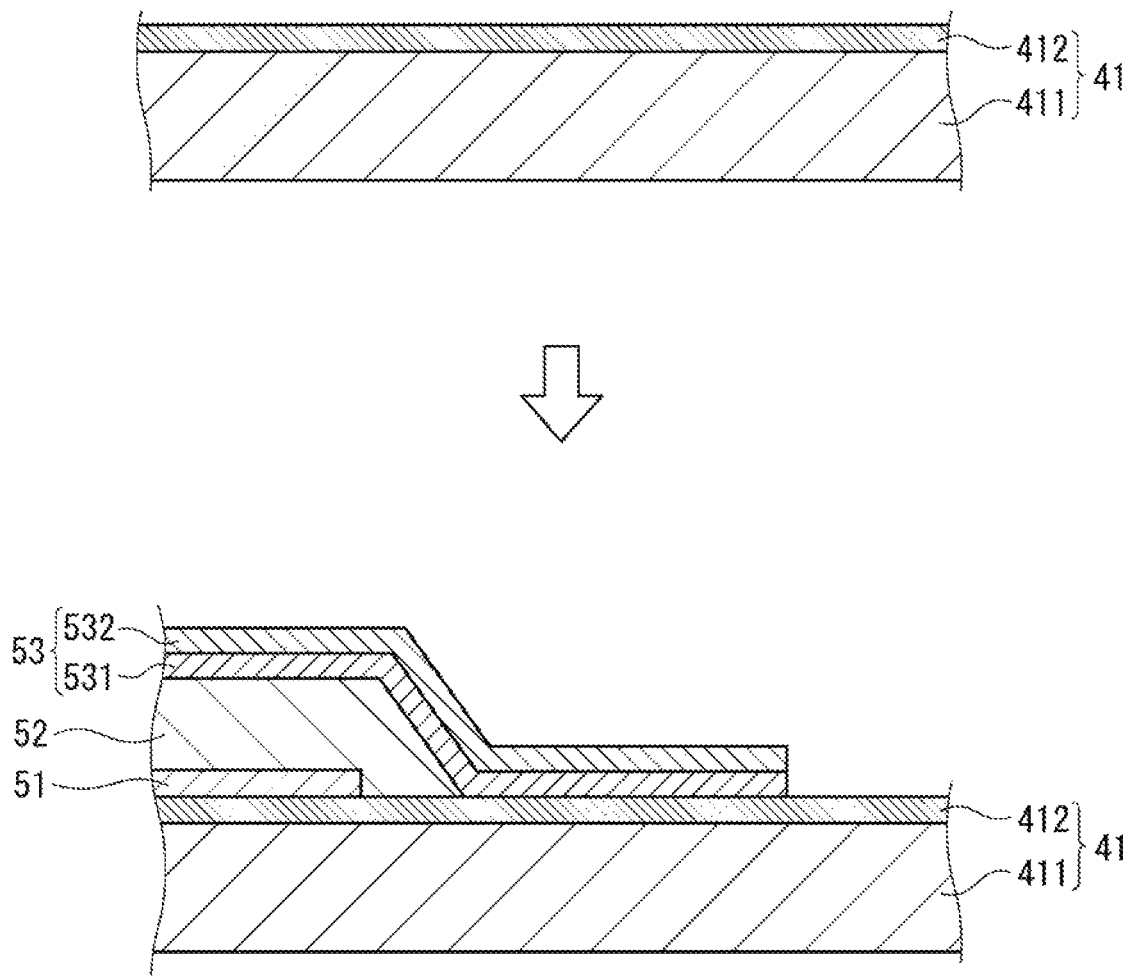
FIG. 10 is a cross-sectional view showing the element formation process shown in FIG. 9.
Figure 11:
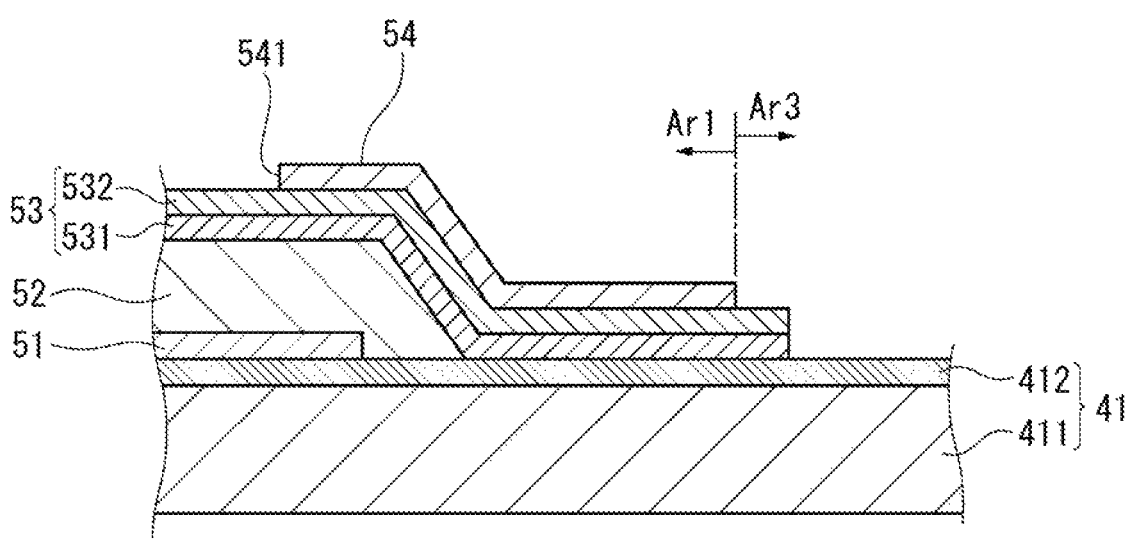
FIG. 11 is a cross-sectional view showing the insulating layer formation process shown in FIG. 9.
Figure 12:
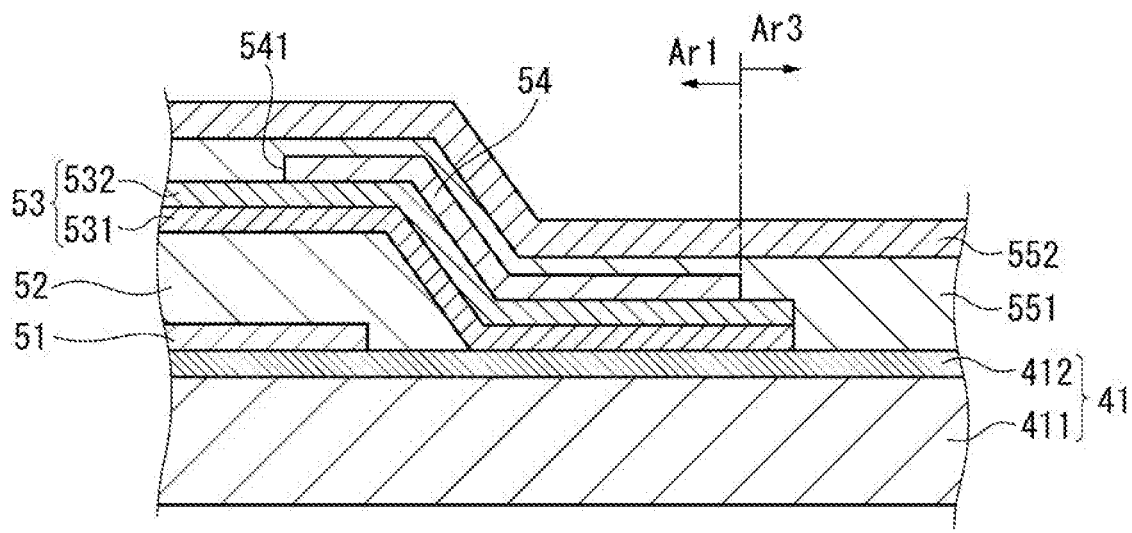
FIG. 12 is a cross-sectional view showing the leading electrode formation process shown in FIG. 9.
Figure 12:
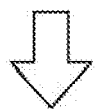
Figure 12:
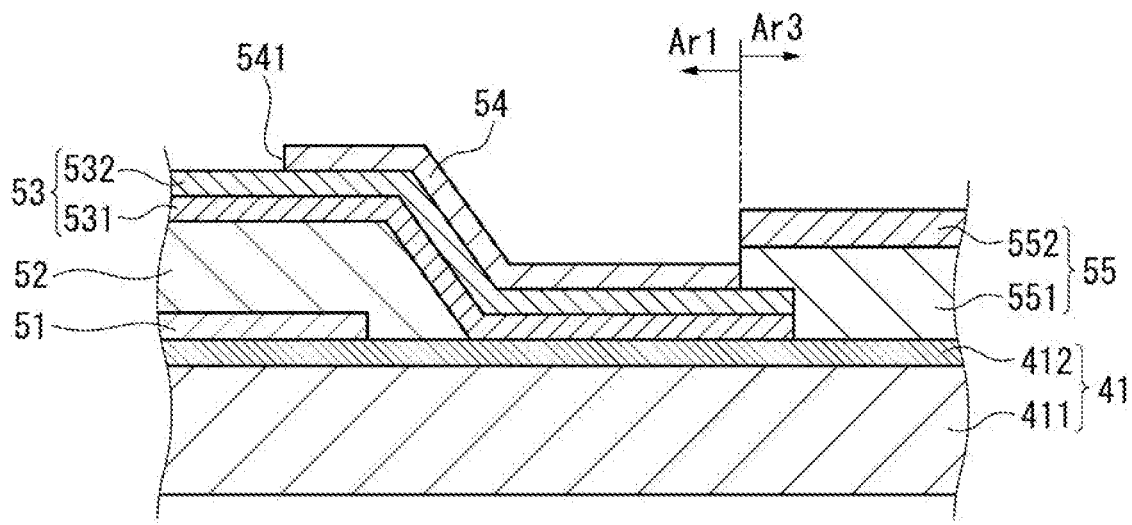

FIG. 10 is a diagram schematically showing the element formation process S11 shown in FIG. 9. FIG. 11 is a diagram schematically showing the insulating layer formation process S12 shown in FIG. 9. FIG. 12 is a diagram schematically showing the leading electrode formation process S13 shown in FIG. 9.

As shown in FIG. 9, in order to manufacture the piezoelectric element 5, the element formation process S11, the insulating layer formation process S12, and the leading electrode formation process S13 are performed.

Element Formation Process

In the element part formation process S11 (element formation process S11), firstly, as shown in a diagram in an upper part of FIG. 10, the vibrating film 412 is formed on the substrate main body part 411 formed of, for example, Si. In the element formation process S11, Zr is deposited on the $SiO_2$ film formed by performing a thermal oxidation process on the substrate main body part 411, and then the thermal oxidation process is further performed to form a $ZrO_2$ layer to thereby form the vibrating film 412.

Subsequently, as shown in a lower part of FIG. 10, the lower electrode 51, the piezoelectric film 52, and the upper electrode 53 are formed on the vibrating film 412.

Specifically, Ir as the formation material of the lower electrode 51 is deposited using, for example, sputtering or a vapor deposition method, and then the Ir metal layer is patterned using etching or the like to form the lower electrode 51.

Then, PZT is formed using, for example, a solution technique. In the formation of PZT using the solution technique, a PZT solution is applied on the vibrating film 412 and the lower electrode 51 (a coating process). Subsequently, the PZT solution having been applied is baked (a calcination process). The calcination process is performed in a condition that, for example, the prebaking temperature is 400° C. and the RTA calcination temperature is 700° C. By repeatedly performing the coating process and the calcination process, the piezoelectric film with a predetermined thickness is formed. Subsequently, PZT thus formed is patterned using an etching process (ion milling) to form the piezoelectric film 52.

Subsequently, Ir constituting the first layer 531 of the upper electrode 53 is deposited on the vibrating film 412, the lower electrode 51, and the piezoelectric film 52 using, for example, sputtering or a vapor deposition method, and further, Ti constituting the second layer 532 is stacked using sputtering or a vapor deposition method. On this occasion, it is preferable to make the thickness of Ti equal to or smaller than 4 nm. Subsequently, the stacked film of the Ir metal layer and the Ti metal layer are patterned using etching or the like to thereby form the upper electrode 53 having the second layer 532 stacked on the first layer 531.

Insulating Layer Formation Process

Then, in the insulating layer formation process S12, for example, liftoff patterns are formed at formation positions of the apertures 541, the terminal apertures 542, and the second terminal area Ar3 on the element substrate 41, and then the layer of $Al_2O_3$ is formed using, for example, atomic layer deposition (ALD). Subsequently, due to the liftoff, by patterning the layer of $Al_2O_3$, there is formed the insulating layer 54 provided with apertures in the areas overlapping the apertures 541, the terminal apertures 542 (not shown in FIG. 11), and the second terminal area Ar3 as shown in FIG. 11.

Incidentally, when forming the layer of $Al_2O_3$ using ALD, an atomic layer deposition device is supplied with TMA ($Al(CH_3)_3$) and $H_2O$, and the layer of $Al_2O_3$ is formed due to the reaction expressed by Formula (1) and Formula (2) described below.

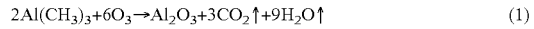

$$2Al(CH_3)_3 + 6O_3 \rightarrow Al_2O_3 + 3CO_2\uparrow + 9H_2O\uparrow \qquad (1)$$

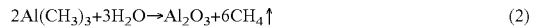

$$2Al(CH_3)_3 + 3H_2O \rightarrow Al_2O_3 + 6CH_4\uparrow \qquad (2)$$

Here, in the reaction expressed by the formulas (1), (2) described above, compounds (i.e., $H_2O$, $CH_4$) including hydrogen are generated, but in the present embodiment, Ti having a high hydrogen occlusion property is used as the second layer 532. Therefore, as a result, hydrogen and the compounds including hydrogen generated in the formulas (1) and (2) are occluded by the second layer 532. Further, if hydrogen or the compounds including hydrogen occluded by the second layer 532 infiltrate the piezoelectric film 52, there is a possibility that the piezoelectric characteristics of the piezoelectric film 52 deteriorate to deteriorate the performance of the piezoelectric element 5.

Figure 13:
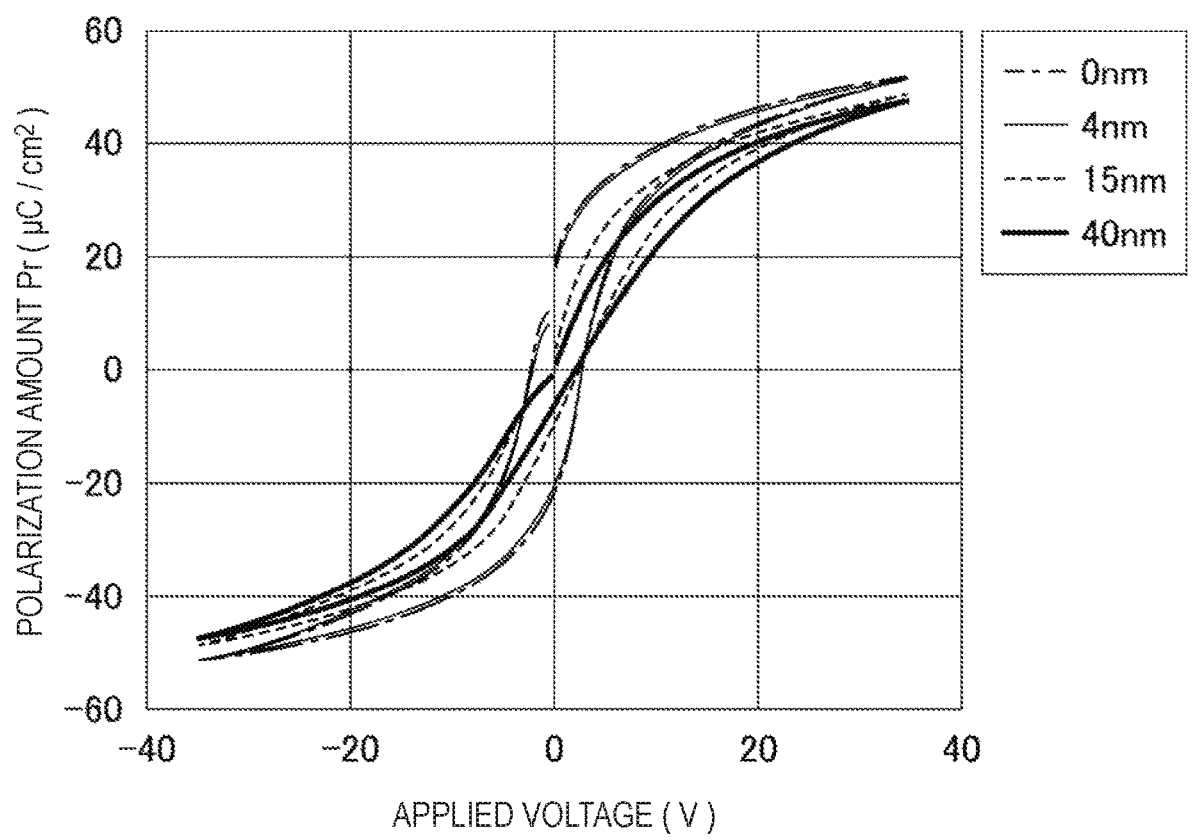
FIG. 13 is a chart showing an example of a relationship between an applied voltage and a polarization amount in a piezoelectric film in the piezoelectric element according to the first embodiment.
Figure 14:
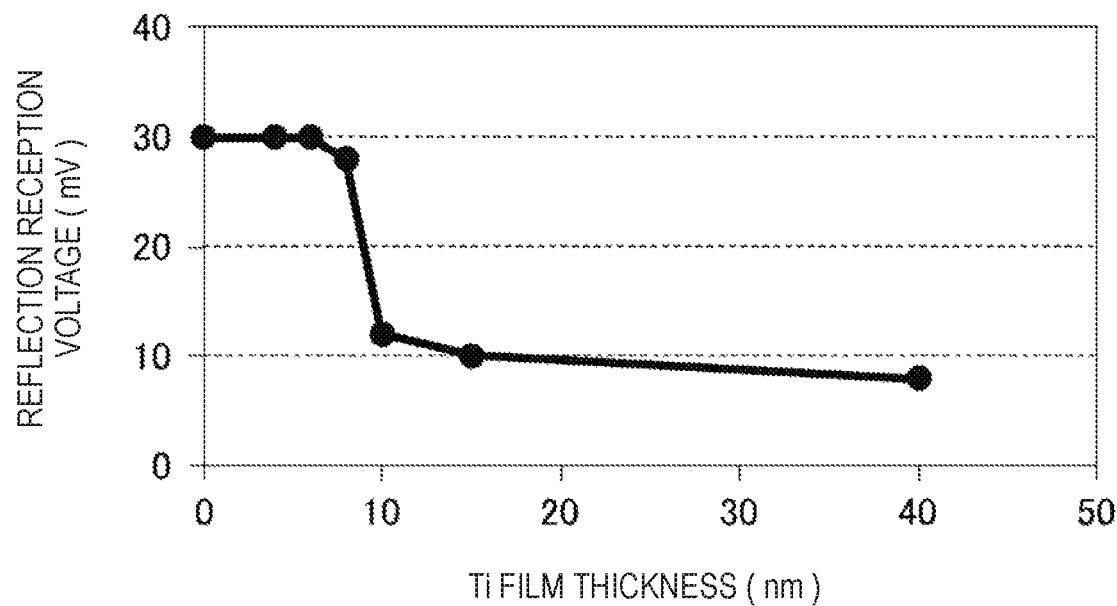
FIG. 14 is a diagram showing an example of a relationship between a thickness of a second layer and a reflection reception voltage in an ultrasonic transducer of the first embodiment.
Figure 15:
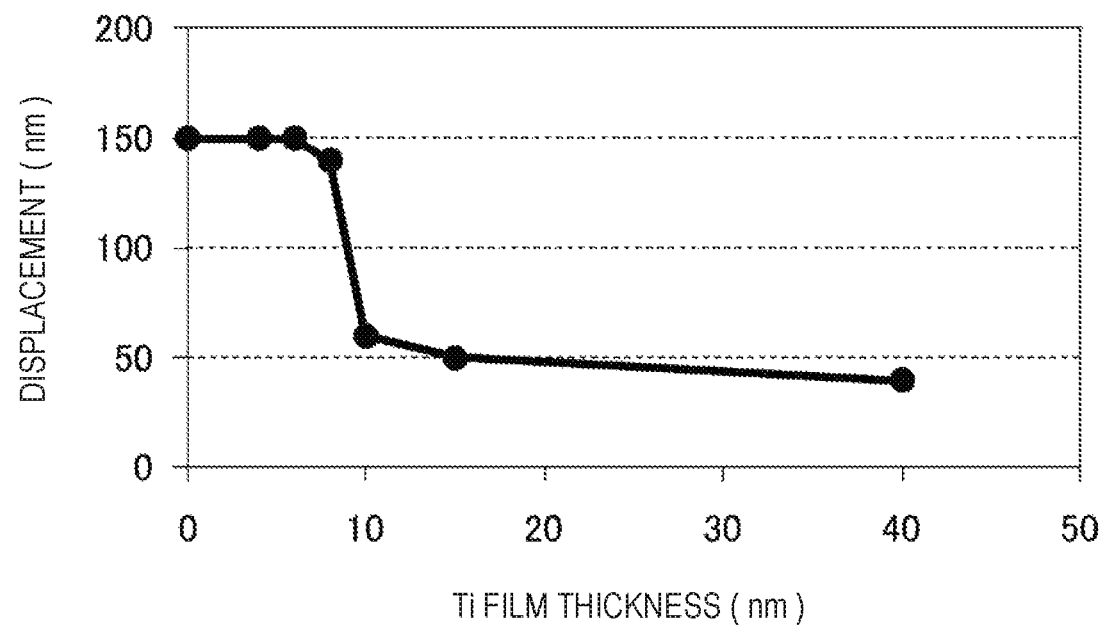
FIG. 15 is a diagram showing an example of a relationship between the thickness of the second layer and a displacement of a piezoelectric layer in the piezoelectric element according to the first embodiment.

FIG. 13 is a chart showing an example of a relationship between an applied voltage and a polarization amount in the piezoelectric film 52 in the piezoelectric element 5 according to the present embodiment. FIG. 14 is a diagram showing an example of a relationship between the thickness of the second layer 532 and a reception voltage (a reflection reception voltage) when receiving the ultrasonic wave in the ultrasonic transducer 45 of the present embodiment. FIG. 15 is a diagram showing an example of a relationship between the thickness of the second layer 532 and a displacement of the piezoelectric element 5 (the piezoelectric film 52) when applying a predetermined voltage in the piezoelectric element 5.

In FIG. 13, in the case in which the thickness of the second layer 532 is 4 nm, the polarization amount and the hysteresis characteristic with respect to the applied voltage are roughly unchanged compared to the case of lacking the second layer 532.

In contrast, as shown in FIG. 13, in the case in which the thickness of the second layer 532 is 15 nm or 40 nm, the polarization amount of the piezoelectric film 52 with respect to the applied voltage decreases, and the hysteresis characteristic with respect to the applied voltage is also deteriorated compared to the case in which the second layer 532 is not provided or the case in which the thickness of the second layer 532 is 4 nm. In other words, the more the thickness of the second layer 532 increases, the more the performance of the piezoelectric element 5 deteriorates. In order to obtain the appropriate polarization amount and the appropriate hysteresis characteristic in the transmission and reception of the ultrasonic wave, the thickness of the second layer 532 is preferably made equal to or smaller than 8 nm, and more preferably made equal to or smaller than 4 nm with which the deterioration of the polarization amount and hysteresis characteristic hardly occurs.

Further, as shown in FIG. 14 and FIG. 15, in the case in which the thickness of the second layer 532 is equal to or smaller than 8 nm, the deterioration of the performance of the piezoelectric element 5 can be suppressed in a favorable manner.

Specifically, as shown in FIG. 14, in the case in which the thickness of the second layer 532 is equal to or smaller than 8 nm, even if the thickness increases, the value of the reflection reception voltage is roughly unchanged. In contrast, if the thickness of the second layer 532 exceeds 8 nm, the value of the reflection reception voltage rapidly drops, and in the case in which the thickness of the second layer 532 becomes equal to or larger than 10 nm, the value of the reflection reception voltage decreases to roughly one third compared to the case in which the thickness is 8 nm.

The same applies to FIG. 15, and in the case in which the thickness of the second layer 532 is equal to or smaller than 8 nm, the displacement of the piezoelectric element 5 in the case of applying a predetermined drive voltage is roughly unchanged. In contrast, if the thickness of the second layer 532 exceeds 8 nm, the displacement of the piezoelectric element 5 is rapidly lowered, and in the case in which the thickness becomes equal to or larger than 10 nm, the displacement decreases to roughly one third compared to the case in which the thickness is 8 nm.

In the present embodiment, in order to suppress such an influence of the thickness of the second layer 532 (Ti) as described above, the second layer 532 is formed to have the thickness equal to or smaller than 4 nm in the element formation process S11. Thus, there is formed the piezoelectric element 5 which is high in performance, and in which deterioration of the reception sensitivity when receiving the ultrasonic wave, reduction of the displacement when applying the drive voltage, and the deterioration of the polarization amount and the hysteresis characteristic with respect to the applied voltage are suppressed. It should be noted that the thickness of the second layer 532 can also be equal to or smaller than 8 nm.

Leading Electrode Formation Process

In the leading electrode formation process S13, as shown in, for example, the upper part of FIG. 12, a NiCr layer and an Au layer are formed in sequence on the element substrate 41 having the lower electrode 51, the piezoelectric film 52, the upper electrode 53, and the insulating layer 54 formed in sequence. Then, by performing patterning using wet etching, the leading electrode 55 is formed as shown in the lower part of FIG. 12.

Here, when performing the wet etching, if the wet etching progresses to the state shown in the lower part in FIG. 12, for example, due to the difference in ionization tendency (i.e., the standard redox potential) between the upper electrode 53 exposed from the aperture 541 and the first leading electrode layer 551, there is a possibility that the electromigration occurs in the first leading electrode layer 551. For example, in the case of adopting the configuration in which the first layer 531 is exposed from the aperture 541, or the case in which the second layer 532 is stacked on the first layer 531, but the insulating layer 54 is not provided, and the first layer 531 is exposed in the side surface of the upper electrode 53, the first layer 531 and the first leading electrode layer 551 have contact with the liquid phase of the etchant. In this case, since the difference (absolute value) in standard redox potential between Ir forming the first layer 531 and NiCr forming the first leading electrode layer 551 is large, there is a possibility that the electromigration may occur in the first leading electrode layer 551 higher in the ionization tendency, and thus, the second leading electrode layer 552 is broken away.

In contrast, in the present embodiment, only the second layer 532 of the upper electrode 53 is exposed in the aperture 541, and the first layer 531 does not have contact with the liquid phase.

Further, a first differential value as a difference in standard redox potential between the metal material (Ti in the present embodiment) forming the second layer 532 and the metal material (NiCr in the present embodiment) forming the first leading electrode layer 551 is made equal to or less than a predetermined first value with which the electromigration of the first leading electrode layer 551 can be suppressed. Further, the first differential value described above is smaller than a second differential value as a difference (absolute value) in standard redox potential between the metal material (Ir in the present embodiment) forming the first layer 531 and the metal material (NiCr in the present embodiment) forming the first leading electrode layer 551.

According to such a configuration, the electromigration of the first leading electrode layer 551 can be suppressed in a favorable manner.

It should be noted that the first value is a value with which the deterioration of the leading electrode 55 can be allowed even if the electromigration occurs in the first leading electrode layer 551, and in the present embodiment, for example, the difference (absolute value) in the standard redox potential is equal to or less than 1.4 V. The first value can be set in view of, for example, etching time, and in the case in which, for example, the etching time is long, it is also possible to use metals closer in standard redox potential as the second metal and the third metal.

Further, the metal material (Ti in the present embodiment) forming the second layer 532 is higher in ionization tendency (lower in standard redox potential) than the metal material (NiCr in the present embodiment) forming the first leading electrode layer 551. Thus, as a result, even in the case in which the electromigration occurs, the second layer 532 seeps into the liquid phase instead of the first leading electrode layer 551. Here, as described above, the smaller the thickness of the second layer 532 is, the more strongly the performance deterioration of the piezoelectric element 5 can be suppressed. Further, the position at which the aperture 541 is disposed is a position overlapping the active section 50 in the plan view, and as the thickness of the second layer 532 decreases, the displacement of the active section 50 also increases. Therefore, if the decrement of the thickness of the second layer 532 due to the electromigration is in an extent in which the first layer 531 is not exposed, it becomes possible to make a contribution to an improvement in performance of the piezoelectric element 5.

Further, the metal material (Au in the present embodiment) forming the second leading electrode layer 552 is lower in ionization tendency (higher in standard redox potential) than the metal materials respectively forming the first layer 531, the second layer 532, and the first leading electrode layer 551. Thus, it is also suppressed to cause the electromigration in the second leading electrode layer 552.

After the above, the substrate apertures 411A are formed on the surface on the opposite side to the vibrating film 412 of the substrate main body part 411 with wet etching using the vibrating film 412 (SiO$_2$) as an etching stopper. According to this process, as shown in FIG. 6, the piezoelectric element 5 with no separation of the leading electrode 55 is formed.

Functions and Advantages of Embodiment

The ultrasonic measurement apparatus 1 according to the present embodiment is provided with the ultrasonic probe 1 and the control device 10, and the ultrasonic probe 2 is provided with the ultrasonic device 22 (the piezoelectric device) provided with the piezoelectric element 5 and the housing 21 for housing the ultrasonic device 22. Further, the piezoelectric element 5 includes the element main body having the lower electrode 51, the piezoelectric film 52, and the upper electrode 53 stacked in sequence, and the leading electrode 55 and the insulating layer 54 stacked on the part located in the second terminal area Ar3 of the upper electrode 53. Further, the insulating layer 54 has the apertures 541 each opening in the area of the active section 50 having the lower electrode 51, the piezoelectric film 52, and the upper electrode 53 stacked on one another on the substrate aperture 411A of the element substrate 41 in the plan view. Further, the insulating layer 54 covers at least the part of the piezoelectric film 52 where the upper electrode 53 is not stacked. Further, the upper electrode 53 includes the first layer 531 constituted by the first metal (Ir in the present embodiment) located on the vibrating film 412 side, and the second layer 532 constituted by the second metal (Ti in the present embodiment) stacked on the first layer 531. Further, the difference (absolute value) in standard redox potential between the second metal and the third metal (NiCr in the present embodiment) constituting the first leading electrode layer 551 of the leading electrode 55 is smaller than the difference (absolute value) in standard redox potential between the first metal and the third metal.

In such a configuration, there is adopted the configuration in which the whole of the piezoelectric film 52 is covered with either the upper electrode 53 or the insulating layer 54, and the deterioration of the piezoelectric film 52 due to burning out or the like can be suppressed.

Further, the second layer 532 of the upper electrode 53 is exposed from the apertures 541 of the insulating layer 54, and the leading electrode 55 is disposed in the part located in the second terminal area Ar3 of the upper electrode 53. Therefore, the first layer 531 of the upper electrode 53 is not exposed to the outside.

Therefore, for example, in the leading electrode formation process S13, even in the case in which the leading electrode 55 and the upper electrode 53 have contact with the liquid phase such as the etchant, the first layer 531 is covered with the second layer 532 or the insulating layer 54, and there do not have contact with the liquid phase, and thus, the electromigration of the first leading electrode layer 551 (NiCr) of the leading electrode 55 can be suppressed. Therefore, an increase in electrical resistance and breaking of the interconnections due to the separation of the second leading electrode layer 552 formed of Au can be prevented. Therefore, when applying a predetermined drive voltage to the piezoelectric element 5, it is possible to appropriately drive the piezoelectric element 5, and thus, it is possible to provide the piezoelectric element 5 high in performance and high in reliability.

Therefore, in the ultrasonic device 22 having such a piezoelectric element 5, it is possible to perform a highly accurate transmission/reception process of an ultrasonic wave. Therefore, in the ultrasonic probe 2 and the ultrasonic measurement apparatus 1 having such an ultrasonic device 22, it is possible to perform a variety of processes such as a highly accurate ultrasonic measurement process, and generation of an internal tomographic image of a living body.

Further, in the piezoelectric element 5, the difference (absolute value) in standard redox potential between the second metal constituting the second layer 532 of the upper electrode 53 and the third metal of the first leading electrode layer 551 is made equal to or less than the first value, with which the deterioration of the leading electrode 55 can be allowed, even if the electromigration occurs in the first leading electrode layer 551.

Thus, it is possible to provide a high performance piezoelectric element in which the increase in resistance and the breaking of the interconnections due to the separation of the second leading electrode layer 552 are suppressed even if some electromigration occurs in the first leading electrode layer 551 due to, for example, etching.

In the present embodiment, the second metal (Ti) of the second layer 532 is higher in ionization tendency (lower in standard redox potential) than the third metal (NiCr) of the first leading electrode layer 551.

Therefore, even in the case in which the electromigration occurs, the second layer 532 is ionized instead of the first leading electrode layer 551 as a result, and therefore, it is possible to suppress the separation and breaking of the interconnections of the second leading electrode layer 552 due to the electromigration of the first leading electrode layer 551.

In addition, the thinner the thickness of the second layer 532 is, the more advantageous to the drive of the active section 50 as shown in FIG. 13, and as shown in FIG. 14 and FIG. 15, by reducing the thickness of Ti as the hydrogen occlusion metal, the characteristic deterioration of the piezoelectric film 52 due to hydrogen is also suppressed. From these points of view, the present embodiment in which the thickness of the second layer 532 is reduced in the case in which the electromigration occurs becomes more advantageous in providing the piezoelectric element 5 high in performance.

In the present embodiment, there are used Ir as the first metal, Ti as the second metal, and NiCr as the third metal.

Ir has superior scientific stability in a broad pH range and a broad temperature range, and is particularly favorable in the case of performing etching when forming the upper electrode 53 (the first layer 531) of the piezoelectric element 5 having a thin-film shape.

Further, in the leading electrode 55, it is preferable to use Au low in electrical resistance as the second leading electrode layer 552. By using NiCr as the first leading electrode 551, the adhesiveness of the second leading electrode layer 552 can be improved using the first leading electrode as the foundation layer.

Further, by using Ti as the second layer 532, it becomes possible to suppress the electromigration of NiCr in a favorable manner even in the case in which the difference (absolute value) in standard redox potential between Ir and NiCr is large.

In the present embodiment, $Al_2O_3$ is used as the insulating layer 54, PZT is used as the piezoelectric film 52, and the thickness of the second layer is equal to or less than 4 nm.

Such an insulating layer using $Al_2O_3$ is superior in insulating property, heat resistance property, and mechanical strength, and is favorable as the insulating layer used for the piezoelectric element. In contrast, in the case of forming the insulating layer made of $Al_2O_3$, hydrogen is generated during the formation in some cases. The hydrogen thus generated is occluded by the second layer 532, and if the hydrogen thus occluded is impregnated by the piezoelectric film 52 formed of PZT, the performance of the piezoelectric element 5 deteriorates. In contrast, in the present embodiment, the second layer 532 is formed to have the thickness equal to or smaller than 4 nm. In this case, as shown in FIG. 14 and FIG. 15, the performance deterioration of the piezoelectric element 5 due to the hydrogen occluded by the second layer 532 can be suppressed.

Second Embodiment

Next, a second embodiment of the invention will be described.

In the first embodiment described above, there is illustrated the configuration of the ultrasonic probe housing the ultrasonic device 22 having the piezoelectric element 5 in the housing 21, and the ultrasonic measurement apparatus 1 equipped with the ultrasonic probe 2 to perform ultrasonic measurement. In contrast, it is possible for the piezoelectric element 5 to be applied to other electronic apparatuses, and in the second embodiment, there will be described a liquid jet apparatus as an example of such other electronic apparatuses.

Figure 16:
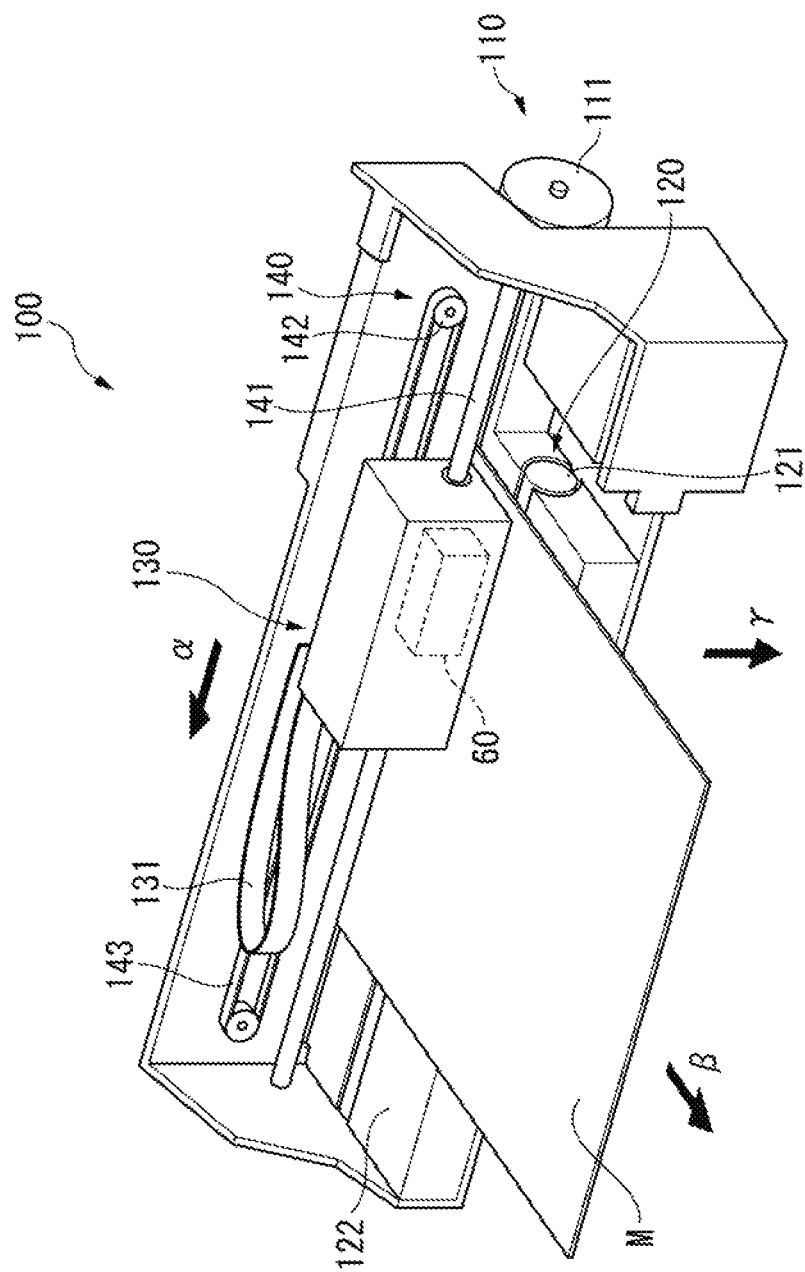
FIG. 16 is a perspective view showing a configuration example of an appearance of a printer according to a second embodiment of the invention.

FIG. 16 is a perspective view showing a configuration example of an appearance of a printer 100 according to the second embodiment.

The printer 100 corresponds to the liquid jet apparatus, and includes a supply 110 for supplying a medium, a conveyor 120 for conveying the medium, a carriage 130 attached with a recording head 60, a carriage mover 140 for moving the carriage 130, and a controller (not shown) for controlling the printer 100 as shown in FIG. 16. The printer 100 controls elements 110, 120, and 140 and the carriage 130 based on print data input from external equipment such as a personal computer to print an image on the medium M.

The supply 110 supplies the medium M at an image formation position. For example, the supply 110 includes a roll body 111 around which the medium M is wound, a roll driving motor (not shown), and a roll driving gear train (not shown). Further, based on a command from the controller, the roll driving motor is rotationally driven, and the rotational force of the roll driving motor is transmitted to the roll body 111 via the roll driving gear train. Thus, the roll body 111 rotates, and a paper sheet wound around the roll body 111 is supplied on the downstream side (+β side) in the β direction (a sub-scanning direction).

The conveyor 120 conveys the medium M supplied from the supply 110 along the β direction. For example, the conveyor 120 includes a conveying roller 121, a driven roller (not shown) disposed across the medium M from the conveying roller 121 to be driven by the conveying roller 121, and a platen 122 disposed on the downstream side in the β direction of the conveying roller 121. The driving force from the roll driving motor not shown is transmitted to the conveying roller 121, and when the roll driving motor is driven by the control of the controller (not shown), the conveying roller 121 is rotationally driven by the rotational force, and the conveying roller 121 conveys the medium M along the β direction in the state of sandwiching the medium M between the driven roller and the conveying roller 121.

The carriage 130 is attached with the recording head 60 for printing the image on the medium M. The recording head is connected to the controller via a cable 131. The recording head 60 will be described later. The carriage 130 is disposed so as to be movable along an α direction (a main scanning direction) crossing the β direction due to the carriage mover 140.

The carriage mover 140 reciprocates the carriage 130 along the α direction. For example, the carriage mover 140 includes a carriage guide shaft 141, a carriage motor 142, and a timing belt 143. The carriage guide shaft 141 is disposed along the α direction, and both ends of the carriage guide shaft 141 are fixed to the housing of the printer 100. The carriage motor 142 drives the timing belt 143. The timing belt 143 is supported roughly in parallel to the carriage guide shaft 141, and a part of the carriage 130 is fixed to the timing belt 143. When the carriage motor 142 is driven based on the command of the controller, the timing belt 143 is made to run forward and backward, and the carriage 130 fixed to the timing belt 143 reciprocates while being guided by the carriage guide shaft 141.

Figure 17:
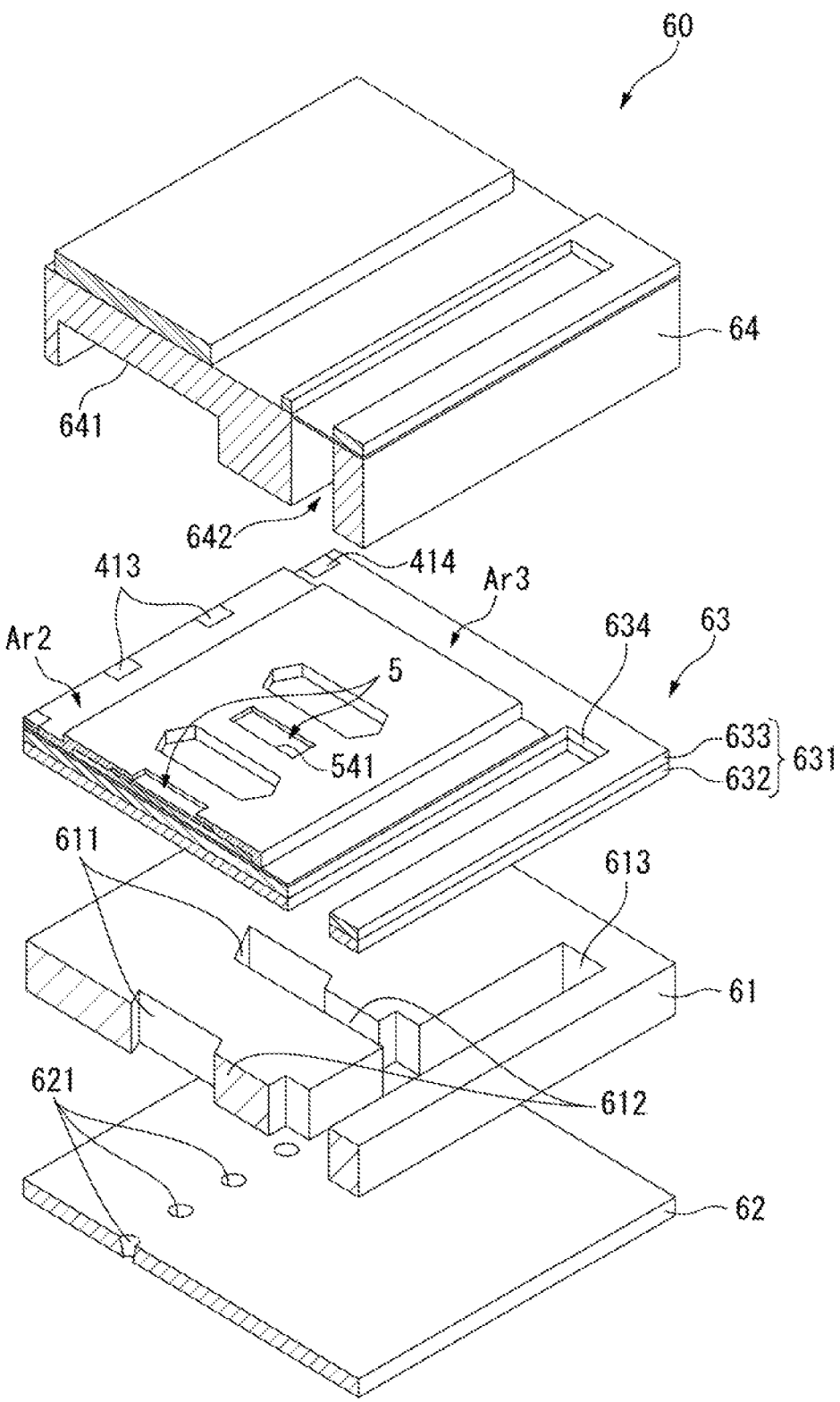
FIG. 17 is an exploded perspective view schematically showing a recording head according to the second embodiment.

FIG. 17 is an exploded perspective view schematically showing the recording head 60.

The recording head 60 corresponds to the liquid jet head, and ejects ink supplied from an ink tank (not shown) toward a y direction crossing the α direction and the β direction to form the image on the medium M. As shown in FIG. 17, the recording head 60 includes a pressure chamber forming substrate 61, a nozzle plate 62, an actuator 63, and a sealing plate 64.

The pressure chamber forming substrate 61 is a plate member formed of, for example, a silicon single-crystal substrate. The pressure chamber forming substrate 61 includes a plurality of pressure chambers 611, ink supply channels 612 for supplying these pressure chambers 611 with the ink, and a communication part 613 communicating with each of the pressure chambers 611 via the respective ink supply channels 612.

The plurality of pressure chambers 611 is disposed so as to correspond one-to-one to the nozzles 621 constituting a nozzle row provided to the nozzle plate 62 as described later. Specifically, the pressure chambers 611 are formed along the nozzle row direction at the same pitch as the formation pitch of the nozzles 621.

The communication part 613 is formed along the plurality of pressure chambers 611. The communication part 613 communicates with a communication aperture 634 of the vibrating plate 631 described later and a liquid chamber space 642 of the sealing plate 64, and is filled with the ink supplied from the ink tank (not shown). The ink with which the communication part 613 is filled is supplied to the pressure chambers 611 via the ink supply channels 612. In other words, the communication part 613 constitutes a reservoir (a common liquid chamber) as an ink chamber common to the pressure chambers 611.

It should be noted that the ink supply channels 612 are each formed to have the width narrower than that of the pressure chamber 611 to function as a flow pass resistance with respect to the ink flowing from the communication part 613 into the pressure chamber 611.

The nozzle plate 62 includes the nozzle row constituted by the plurality of nozzles 621, and is bonded to one surface (a surface on the opposite side to the actuator 63) of the pressure chamber forming substrate 61. The plurality of nozzles 621 is formed at the pitch corresponding to the dot formation density (e.g., 300 dpi). It should be noted that the nozzle plate 62 is formed of, for example, glass ceramics, a silicon single-crystal substrate, or stainless steel.

The actuator 63 is configured including the vibrating plate 631 disposed on the opposite side to the nozzle plate 62 of the pressure chamber forming substrate 61, and the piezoelectric elements 5 stacked on the vibrating plate 631.

The vibrating plate 631 includes an elastic film 632 formed on the pressure chamber forming substrate 61, and an insulator film 633 formed on the elastic film 632. It should be noted that as the elastic film 632, there is preferably used, for example, silicon dioxide ($SiO_2$) having the thickness of 300 through 2000 nm. Further, as the insulator film 633, there is preferably used, for example, zirconium oxide ($ZrO_x$) having the thickness of 30 through 600 nm. The area for blocking the pressure camber 611 of the vibrating plate 631 is an area (a flexible part) allowed to make a distortional deformation in the direction of coming closer to and getting away from the nozzle 621 due to the drive of the piezoelectric element 5. It should be noted that the part corresponding to the communication part 613 of the pressure chamber forming substrate 61 in the vibrating plate 631 includes a communication aperture 634 communicating with the communication part 613.

Although not shown in the drawings, the piezoelectric elements 5 each have substantially the same configuration as in the first embodiment described above, and are each provided with an element main body having the lower electrode 51, the piezoelectric film 52, and the upper electrode 53 stacked in sequence on one another, the insulating layer 54, and the leading electrode 55. The piezoelectric element 5 is disposed at the position corresponding to the pressure chamber 611 to constitute the piezoelectric actuator together with the flexible part as the area blocking the pressure chamber 611 of the vibrating plate 631 (the drive section). Further, as shown in FIG. 17, the signal terminals 413 electrically connected to the lower electrodes 51 are disposed in the first terminal area Ar2 on the vibrating plate 631, and the common terminal 414 electrically connected to the upper electrodes 53 is disposed in the second terminal area Ar3.

Here, although in FIG. 17, the configuration of the piezoelectric element 5 is illustrated in a simplified manner, the aperture 541 is also formed at the position overlapping the active section 50 in the plan view viewed from the thickness direction of the vibrating plate 631 of the insulating layer 54 to expose the second layer 532 of the upper electrode 53 in the present embodiment. Further, the upper electrodes 53 are each disposed so as to extend to the second terminal area Ar3, and are connected to the leading electrode 55 in the second terminal area Ar3.

The sealing plate 64 is bonded to the surface on the opposite side to the pressure chamber forming substrate 61 of the actuator 63. On the surface located on the actuator 63 side of the sealing plate 64, there is formed a housing 641 capable of housing the piezoelectric elements 5. Further, in an area corresponding to the communication aperture 634 and the communication part 613 of the sealing plate 64, there is disposed the liquid chamber space 642. The liquid chamber space 642 communicates with the communication aperture 634 and the communication part 613 to constitute the reservoir functioning as the ink chamber common to the pressure chambers 611. It should be noted that although not shown in the drawings, the sealing plate 64 includes a wiring aperture penetrating in the thickness direction at a position corresponding to the terminal areas of the actuator 63. In the wiring aperture, there are exposed the electrode terminals in the terminal areas described above. These electrode terminals are connected to wiring members not shown connected to the printer main body.

In the recording head 60 having such a configuration, the ink is introduced from an ink cartridge to fill the reservoir, the ink supply channels 612, the pressure chambers 611, and the flow channels to the nozzles 621 with the ink. Then, when the piezoelectric elements 5 corresponding respectively to the pressure chambers 611 are driven due to the supply of the drive signal from the printer main body, the areas (the flexible parts) corresponding to the pressure chambers 611 of the vibrating plate 631 are displaced to cause pressure variations in the respective pressure chambers 611. By controlling the pressure variations, the ink is ejected from the respective nozzles 621.

Functions and Advantages of Second Embodiment

In the second embodiment configured in such a manner as described above, similarly to the first embodiment, in each of the piezoelectric elements 5, the second layer 532 of the upper electrode 53 is exposed from the aperture 541 of the insulating layer 54, and the leading electrode 55 is disposed in the part located in the second terminal area Ar3 of the upper electrode 53. Therefore, in the formation of the piezoelectric element 5, even in the case in which the leading electrode 55 and the upper electrode 53 have contact with the liquid phase, the increase in electrical resistance and the breaking of the interconnections due to the separation of the leading electrode 55 can be suppressed. Thus, it is possible to suppress the performance deterioration of the recording head 60 and the printer 100 equipped with the piezoelectric elements 5, and thus, it is possible to achieve highly accurate liquid jet processing.

Modified Examples

In the embodiment described above, there is illustrated the configuration using Ir as the first metal for forming the first layer 531, Ti as the second metal for forming the second layer 532, and NiCr as the third metal for forming the first leading electrode layer 551. However, each of the first metal, the second metal, and the third metal is not limited to the metal illustrated in the embodiment described above. For example, the first metal can also be one species selected from a group consisting of iridium, platinum, and gold, or an alloy of two or more species selected from the group. Further, the second metal can also be one species selected from a group consisting of titanium, zirconium, manganese, tantalum, and zinc, or an alloy of two or more species selected from the group. Further, the third metal can also be one species selected from a group consisting of nickel, chromium, iron, cadmium, and cobalt, or an alloy of two or more species selected from the group.

In other words, as the second metal, it is possible to use a metal material which satisfies the condition that the difference (absolute value) in standard redox potential between the metal material and the third metal is smaller than the difference (absolute value) in standard redox potential between the first metal and the third metal. Thus, it is possible to suppress the electromigration of the first leading electrode 551 formed of the third metal compared to the configuration of making the first leading electrode layer 551 formed of the third metal have contact with the first electrode 531 formed of the first metal.

Further, the second metal and the third metal having the difference (absolute value) in standard redox potential equal to or less than the first value can be used. Thus, the electromigration of the first leading electrode layer 551 can be suppressed. It should be noted that it is preferable to use a metal material having good adhesiveness with the constituent material of the second leading electrode layer 552 as the third metal. Thus, the separation of the second leading electrode layer 552 can be suppressed in a favorable manner.

In the embodiment described above, there is illustrated the second layer 532 formed using the second metal higher in ionization tendency (lower in standard redox potential) than the third metal, but this is not a limitation. For example, it is also possible to use the second metal lower in ionization tendency than the third metal (higher in standard redox potential than the third metal). Even in this case, by making the difference (absolute value) between the second metal and the third metal equal to or smaller than the first value, the electromigration of the first leading electrode layer 551 can be suppressed. It is also possible to use, for example, Ti as the second metal and Al as the third metal.

Although the example using Ti as the second metal is described, this is not a limitation, and it is also possible to use other metal which satisfies the condition that the difference (absolute value) in standard redox potential from the third metal is equal to or smaller than the first value. In this case, it is preferable to use the metal poor in hydrogen occlusion property as the second metal. In the case of the metal having the hydrogen occlusion property, it is formed so as to have the film thickness with which the influence of the hydrogen thus occluded on the piezoelectric film 52 can be suppressed.

In the embodiment described above, there is illustrated the case of using Ir as the first metal, but this is not a limitation. It is possible to use the metal material and the electrically conductive oxide having the difference in standard redox potential with respect to the second metal and the third metal satisfying the relationship described above.

In the embodiment described above, the first leading electrode layer 551 and the second leading electrode layer 552 are deposited, and then the leading electrode 55 is patterned by etching in the leading electrode formation process S13. In contrast, it is also possible to pattern the first leading electrode layer 551 by etching after forming the first leading electrode layer 551, and then form the second leading electrode layer 552.

Further, the substrate apertures 411A are formed after the element formation process S11, the insulating layer formation process S12, and the leading electrode formation process S13, but it is also possible to form the substrate apertures 411A in, for example, the element formation process S11.

In the embodiment described above, there is described the example in which the insulating layer 54 is formed from the boundary between the array area Ar1 and the second terminal area Ar3 toward the array area Ar1, and the leading electrode 55 is formed from the boundary between the array area Ar1 and the second terminal area Ar3 toward the second terminal area Ar3 as shown in FIG. 6. In contrast, it is also possible for a part of the leading electrode 55 to be formed so as to overlap the array area Ar1. In this case, the side surface (the side surface crossing the surface on the vibrating film 412 side) of the first layer 531 of the upper electrode 53 is not exposed in the boundary between the array area Ar1 and the second terminal area Ar3, and it is possible to more surely suppress the exposure of the first layer 531 and the electromigration of the third metal due to the exposure.

Although in the first embodiment described above, there is described the example in which the leading electrode 55 is formed of the first leading electrode layer 551 and the second leading electrode layer 552, it is also possible for the leading electrode 55 to be formed of one layer alone including the third metal. Further, the leading electrode 55 can also be formed of three or more metal layers.

Although $Al_2O_3$ is illustrated as the insulating layer 54, this is not a limitation, and it is also possible to use metal oxide having an insulating property such as $TaO_x$ or $BaO_x$.

In the embodiment described above, as the ultrasonic transducers 45, there is described the example in which the sealing plate 42 is disposed on the vibrating film 412 side of the element substrate 41, the ultrasonic wave is transmitted from the substrate aperture 411A of the element substrate 41, and the ultrasonic wave entering from the substrate aperture 411A is received, but this is not a limitation. For example, it is also possible to adopt a configuration in which the sealing plate 42 is disposed on the opposite side to the vibrating film 412 of the element substrate 41, the ultrasonic wave is transmitted toward the opposite side to the substrate aperture 411A, and the ultrasonic wave entering from the opposite side to the substrate aperture 411A is received.

In the embodiment described above, the shape and the area of the flexible part 412A in the vibrating film are defined by the substrate aperture 411A provided to the substrate main body part 411, but this is not a limitation. For example, an element aperture having a linear shape parallel to the Y direction is provided to the substrate main body part 411. Then, there is adopted a configuration in which a plurality of beam parts for bonding the sealing plate 42 and the vibrating film 412 to each other is disposed in the X direction, and the element aperture is divided by the beam parts into a plurality of areas. In this case, each of the areas (the areas surrounded by the element aperture and the beam parts) thus divided into constitutes the flexible part, and it is sufficient to dispose the piezoelectric elements 5 so that the active sections are located in the respective flexible parts.

Besides the above, specific structures to be adopted when implementing the invention can be configured by arbitrarily combining the embodiments and the modified examples described above with each other, or can arbitrarily be replaced with other structures within the range in which the advantages of the invention can be achieved.

The entire disclosure of Japanese Patent Application No. 2017-061440 filed Mar. 27, 2017 is expressly incorporated herein by reference.

What is claimed is:

1. A piezoelectric element comprising:
    a first electrode layer;
    a piezoelectric layer stacked on the first electrode layer;
    a second electrode layer stacked on the piezoelectric layer, the second electrode layer having a first layer and a second layer, the second layer being stacked on the first layer, the first layer including first metal, the a second layer including second metal;
    a third electrode layer stacked on a part of the second electrode layer, the third electrode layer including third metal; and
    an insulating layer on the second electrode layer and covering at least a part of the piezoelectric layer that is not provided with the second electrode layer, the insulating layer having an aperture exposing apart of the second electrode layer, wherein the second layer of the second electrode layer is exposed in the aperture, and a difference in standard redox potential between the second metal and the third metal is smaller than a difference in standard redox potential between the first metal and the third metal.

2. The piezoelectric element according to claim 1, wherein
the difference in standard redox potential between the second metal and the third metal is one of equal to and smaller than 1.4 V.

3. The piezoelectric element according to claim 1, wherein
the second metal is lower in standard redox potential than the third metal.

4. The piezoelectric element according to claim 1, wherein
the first metal is one species selected from the group consisting of iridium, platinum, gold, and alloys thereof,
the second metal is one species selected from the group consisting of titanium, zirconium, manganese, tantalum, zinc, and alloys thereof, and
the third metal is one species selected from the group consisting of nickel, chromium, iron, cadmium, cobalt, and alloys thereof.

5. The piezoelectric element according to claim 1, wherein
the first metal is iridium,
the second metal is titanium, and
the third metal is an alloy of nickel and chromium.

6. The piezoelectric element according to claim 5, wherein
the insulating layer is aluminum oxide,
the piezoelectric layer is metal oxide having ferroelectricity, and
the second layer is less than 8 nm thick.

7. A piezoelectric device comprising:
a piezoelectric element including:
a first electrode layer;
a piezoelectric layer stacked on the first electrode layer;
a second electrode layer stacked on the piezoelectric layer, the second electrode layer having a first layer and a second layer, the second layer being stacked on the first layer, the first layer including first metal, the a second layer including second metal;
a third electrode layer stacked on a part of the second electrode layer, the third electrode layer including third metal; and
an insulating layer covering at least a part of the piezoelectric layer that is not provided with the second electrode layer, the insulating layer having an aperture exposing a part of the second electrode layer,
wherein the second layer of the second electrode layer is exposed in the aperture, and
a difference in standard redox potential between the second metal and the third metal is smaller than a difference in standard redox potential between the first metal and the third metal; and
a drive section driven by the piezoelectric element.

8. The piezoelectric device according to claim 7, wherein
the difference in standard redox potential between the second metal and the third metal is one of equal to and smaller than 1.4 V.

9. The piezoelectric device according to claim 7, wherein
the second metal is lower in standard redox potential than the third metal.

10. The piezoelectric device according to claim 7, wherein
the first metal is one species selected from the group consisting of iridium, platinum, gold, and alloys thereof,
the second metal is one species selected from the group consisting of titanium, zirconium, manganese, tantalum, zinc, and alloys thereof, and
the third metal is one species selected from the group consisting of nickel, chromium, iron, cadmium, cobalt, and alloys thereof.

11. The piezoelectric device according to claim 7, wherein
the first metal is iridium,
the second metal is titanium, and
the third metal is an alloy of nickel and chromium.

12. The piezoelectric device according to claim 11, wherein
the insulating layer is aluminum oxide,
the piezoelectric layer is metal oxide having ferroelectricity, and
the second layer is less than 8 nm thick.

13. The piezoelectric device according to claim 7, wherein
the drive section is a vibrating film.

14. An ultrasonic probe comprising:
a piezoelectric device including:
a first electrode layer;
a piezoelectric layer stacked on the first electrode layer;
a second electrode layer stacked on the piezoelectric layer, the second electrode layer having a first layer and a second layer, the second layer being stacked on the first layer, the first layer including first metal, the a second layer including second metal;
a third electrode layer stacked on a part of the second electrode layer, the third electrode layer including third metal; and
an insulating layer covering at least a part of the piezoelectric layer that is not provided with the second electrode layer, the insulating layer having an aperture exposing a part of the second electrode layer,
wherein the second layer of the second electrode layer is exposed in the aperture, and
a difference in standard redox potential between the second metal and the third metal is smaller than a difference in standard redox potential between the first metal and the third metal;
a vibrating film driven by the piezoelectric element; and
a housing holding the piezoelectric device.

15. The ultrasonic probe according to claim 14, wherein
the difference in standard redox potential between the second metal and the third metal is one of equal to and smaller than 1.4 V.

16. The ultrasonic probe according to claim 14, wherein
the second metal is lower in standard redox potential than the third metal.

17. The ultrasonic probe according to claim 14, wherein
the first metal is one species selected from the group consisting of iridium, platinum, gold, and alloys thereof,
the second metal is one species selected from the group consisting of titanium, zirconium, manganese, tantalum, zinc, and alloys thereof, and the third metal is one species selected from the group consisting of nickel, chromium, iron, cadmium, cobalt, and alloys thereof.

18. The ultrasonic probe according to claim 14, wherein
the first metal is iridium,
the second metal is titanium, and
the third metal is an alloy of nickel and chromium.

19. The ultrasonic probe according to claim 18, wherein
the insulating layer is aluminum oxide,
the piezoelectric layer is metal oxide having ferroelectricity, and
the second layer is less than 8 nm thick.

20. The ultrasonic probe according to claim 14 further comprising:
a controller configured to control the piezoelectric device.

* * * * *